United States Patent [19]

Koga et al.

[11] Patent Number: 5,646,308

[45] Date of Patent: Jul. 8, 1997

[54] BENZOPYRAN DERIVATIVES

[75] Inventors: Hiroshi Koga; Hiroyuki Nabata, both of Shizuoka, Japan

[73] Assignee: Chugai Seiyaku Kabushiki Kaisha, Tokyo, Japan

[21] Appl. No.: 256,580

[22] PCT Filed: Jan. 25, 1993

[86] PCT No.: PCT/JP93/00086

§ 371 Date: Jul. 18, 1994

§ 102(e) Date: Jul. 18, 1994

[87] PCT Pub. No.: WO93/15068

PCT Pub. Date: Aug. 5, 1993

[30] Foreign Application Priority Data

Jan. 24, 1992 [JP] Japan ..................... 4-010819

[51] Int. Cl.$^6$ ..................... C07D 311/58
[52] U.S. Cl. ............ 549/404; 549/343; 549/344; 549/399; 549/405; 549/407
[58] Field of Search ............... 549/13, 343, 344, 549/399, 404, 405, 407; 514/456

[56] References Cited

U.S. PATENT DOCUMENTS 4,415,741  11/1983  Kabbe .................. 549/344
5,412,117  5/1995  Koga et al. ............ 549/399

FOREIGN PATENT DOCUMENTS 0398665  11/1990  European Pat. Off. .

Primary Examiner—Ba K. Trinh
Attorney, Agent, or Firm—Browdy and Neimark

[57] ABSTRACT

Benzopyran derivatives represented by formula (I):

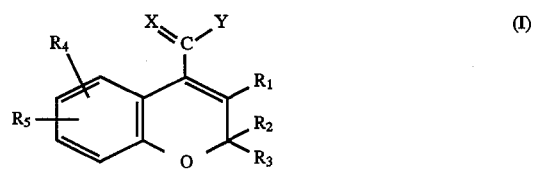

wherein X represents =O, =S, =N—Z, etc. (Z represents a lower alkyl group, etc.); Y represents a substituted amino group, an alkoxy group, an alkylthio group, etc., and $R_1$, $R_2$, $R_3$, $R_4$ and $R_5$ each represents a hydrogen atom, a lower alkyl group, etc, are disclosed. The benzopyran derivative exhibit $K^+$ channel opening activities and are widely applicable as antiasthmatics, antiepileptics, and the like.

7 Claims, No Drawings

BENZOPYRAN DERIVATIVES

This application is a 371 of PCT/JP93/00086, dated Jan. 25, 1993.

FIELD OF THE INVENTION

The present invention relates to a novel benzopyran derivative which is useful as medicine.

PRIOR ART

Benzopyran derivatives having various pharmacological effects have been known. For example, various benzopyran derivatives in which the 4-position carbon atom of a benzopyran ring is directly linked to a nitrogen atom are disclosed in Japanese Laid-Open Patent Publications No. 97974/1985, No. 47416/1986, No. 165317/1988, No. 196581/1988, No. 201182/1988, No. 303977/1988, No. 26578/1989, No. 38087/1989, No. 129184/1990 and Journal of Medicinal Chemistry, Vol. 33, No. 6, pp. 1529–1541, 1990. In the above documents there is described that said compounds have an anti-hypertension effect and can be used for a treatment for heart diseases.

Among the benzopyran derivatives disclosed in the above documents, Cromakalim represented by the following formula has recently been remarked as a new kind of a hypotensive drug having an effect on $K^+$ channel together with Nicorandil and Pinacidil.

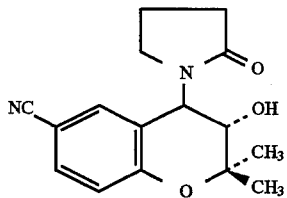

Besides, derivatives in which the 4-position carbon atom of a benzopyran ring is not directly linked to a nitrogen atom are also disclosed in Japanese Laid-Open Patent Publications No. 303977/1988 and No. 38087/1989, Official Gazette of WO 90/14346, Journal of Heterocyclic Chemistry, Vol. 11 (5), pp. 797–802, 1974 and Journal of Medicinal Chemistry, Vol. 33, No. 6, pp. 1529–1541, 1990. Particularly, in the Official Gazette of WO 90/14346 is disclosed a similar compound to the compound containing an amide group or a thioamide group at the 4-position of a benzopyran ring of the present invention.

The present inventors have studied assiduously about the synthesis of a benzopyran derivative which has the equivalent or more excellent $K^+$ channel opening activities than said similar compound and Cromakalim and in which the 4-position carbon atom of a benzopyran ring is not directly linked to a nitrogen atom and about $K^+$ channel effect activities. As a result, they have found that a novel benzopyran derivative to be described below, which is disclosed in no document, has such pharmacological activities and accomplished the present invention on the basis of this finding.

DISCLOSURE OF THE INVENTION

The compound of the present invention is a novel compound represented by the following general formula (I) having excellent $K^+$ channel opening activities:

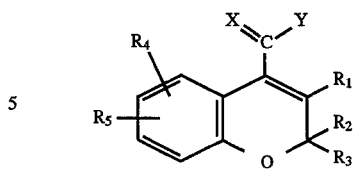

wherein $R_1$ represents a hydrogen atom or a hydroxyl group, $R_2$ and $R_3$ represent, in common with each other or independently, a lower alkyl group, a substituted lower alkyl group containing a halogen atom or a lower alkoxy group as a substituent, or, in combination, a heterocycle containing an oxygen atom or a sulfur atom as a hetero atom; $R_2$ and $R_3$ do not represent a lower alkyl group simultaneously, though, $R_4$ and $R_5$ represent, in common with each other or independently, a hydrogen atom, a lower alkyl group, a lower haloalkyl group, a halogen atom, a lower alkoxy group, a lower haloalkoxy group, an amino group, an acylamino group, a nitro group, a cyano group, an ester group, a lower alkylsulfonyl group or an arylsulfonyl group.

X represents $=O$, $=S$ or $=N-Z$, wherein Z represents a hydrogen atom, a lower alkyl group, an aryl group, a hydroxy group, a lower alkoxy group, a cyano group, a carbamoyl group or a sulfamoyl group, and Y represents $-NR_6R_7$, $-OR_8$ or $-SR_9$, wherein $R_6$ and $R_7$ represent, in common with each other or independently, a hydrogen atom, a hydroxyl group, a lower alkoxy group, a cyano group, an optionally substituted amino group, a saturated or unsaturated lower alkyl group which is optionally substituted, an optionally substituted aryl group, an optionally substituted cycloalkyl group, an optionally substituted heteroaryl group, or $R_6$ and $R_7$, in combination, represent a heterocycle optionally substituted with a nitrogen atom, and $R_8$ and $R_9$ represent a hydrogen atom, a lower alkyl group or an aryl group.

In the definition of the compounds represented by the general formula (I), a lower alkyl group means an alkyl group having 1 to 6 carbon atoms, preferably 1 to 4 carbon atoms. Examples of such a lower alkyl group include a methyl group, an ethyl group, an n-propyl group, an i-propyl group, an n-butyl group, an i-butyl group, an s-butyl group, and a t-butyl group.

A lower alkoxy group means an alkoxy group having 1 to 6 carbon atoms. Examples of such a lower alkoxy group include a methoxy group, an ethoxy group, an n-propoxy group, an i-propoxy group, an n-butoxy group, an i-butoxy group, an s-butoxy group and a t-butoxy group.

A halogen atom means chlorine, fluorine, bromine and iodine, preferably chlorine and fluorine.

As a substituted lower alkyl group containing a halogen atom or a lower alkoxy group as a substituent there can be mentioned, for example, a methoxymethyl group and a fluoromethyl group.

As a heterocycle containing an oxygen atom or a sulfur atom there as a hereto atom can be mentioned, for example, a tetrahydropyranyl group and a tetrahydrothiopyranyl group.

As an acylamino group there can be mentioned, for example, lower alkylcarboxylic acid amino groups such as an acetylamino group, a propionic acid amino group, a butylic acid amino group and a valerianic acid amino group.

As an ester group there can be mentioned, for example, lower alkyl ester groups such as a methyl ester group, an ethyl ester group, a propyl ester group and a butyl ester group.

As a lower alkylsulfonyl group there can be mentioned, for example, a methylsulfonyl group, an ethylsulfonyl group, a propylsulfonyl group and a butylsulfonyl group.

As an arylsulfonyl group there can be mentioned, for example, a phenylsulfonyl group, a naphtylsulfonyl group, a tolylsulfonyl group, a xylylsulfonyl group and a biphenyl-sulfonyl group.

As an optionally substituted cycloalkyl group there can be mentioned, for example, a cyclopropyl group substituted with a halogen atom or a lower alkyl group, a cyclobutyl group, a cyclopentyl group and a cyclohexyl group.

As an optionally substituted heteroaryl group there can be mentioned, for example, aryl groups containing a hereto atom such as a pyridyl group, a pyrimidinyl group, a quinolinyl group, a pyrazinyl group, a thiazoyl group, an oxazolyl group, an imidazoyl group, a thiadiazole group and a tetrazolyl group.

The compound represented by the general formula (I) can be produced, for example, by reacting a compound represented by the general formula (III):

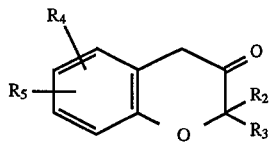

wherein $R_2$, $R_3$, $R_4$ and $R_5$ mean as defined above, with a compound represented by the general formula (IV):

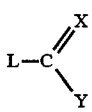

wherein

X and Y mean as defined above, and

L represents a halogen atom, or an eliminating group such as —$OR_{10}$ or —$SOnR_{11}$, wherein $R_{10}$ and $R_{11}$ represent a hydrogen atom, a lower alkyl group or an aryl group, and n represents 0 or an integer of 1 or 2, in an inactive solvent in the presence of a base.

As a base to be used herein there can be mentioned, for example, sodium hydride, sodium alkoxide, potassium alkoxide, alkyl lithium, potassium carbonate, sodium carbonate, potassium hydroxide or sodium hydroxide.

In addition, the compound represented by the above general formula (I) of the present invention can also be obtained by reacting a compound represented by the above general formula (III) with a compound represented by the general formula (V):

wherein

X means as defined above, and

W represents an oxygen atom, a sulfur atom or N—$R_{12}$, wherein $R_{12}$ has the same meaning as $R_6$ or $R_7$. As a compound represented by the general formula (V) there can be mentioned, for example, methyl isothiocyanate.

The compound represented by the above general formula (I) can also be obtained by dehydrating a compound represented by the general formula (VII):

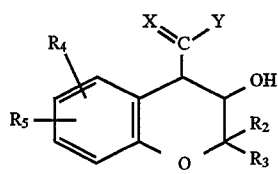

wherein

X, Y, $R_2$, $R_3$, $R_4$ and $R_5$ mean as defined above, said compound represented by the general formula (VII) obtained by reducing a compound represented by the general formula (VI):

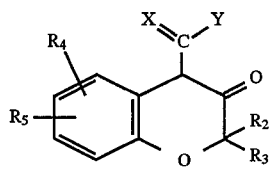

wherein

X, Y, $R_2$, $R_3$, $R_4$ and $R_5$ mean as defined above.

A reduction reaction is carried out by the action of a reducing agent, for example, boron hydride such as $NaBH_4$, $KBH_4$, $LiBH_4$, $NaBH_3CN$ and $LiAlH$ or metal hydrides in an inactive solvent, or by catalytic reduction using palladium carbon or Raney nickel.

A dehydration reaction is carried out by using an acid such as paratoluenesulfonic acid and hydrogen chloride in an inactive solvent, or by using an acid halide such as para-toluenesulfonyl chloride and acetyl chloride or an anhydride such as acetic anhydride in the presence of a base. As a base to be used here there can be mentioned organic bases such as pyridine and triethylamine, or sodium hydroxide, sodium alkoxide, potassium alkoxide, alkyl lithium, potassium carbonate, sodium carbonate, potassium hydroxide and sodium hydroxide.

The compound represented by the above general formula (I) can also be obtained by reacting a compound represented by the general formula (VIII):

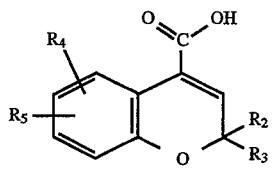

wherein $R_2$, $R_3$, $R_4$ and $R_5$ mean as defined above, with $HNR_6R_7$, wherein $R_6$ and $R_7$ mean as defined above, in an inactive solvent by using a suitable condensation agent.

As a condensation agent to be used herein there can be mentioned, for example, amido reagents such as carbonyl di-imidazole, triphenylphosphine and 2,2'-dipyridyl disulfide.

Moreover, the compound represented by the general formula (I) of the present invention can also be obtained according to concrete methods of production described in Examples.

The compound represented by the general formula (I) of the present invention exhibits, as apparent from Examples to be described later, excellent $K^+$ channel opening effects and can be used as smooth muscle relaxation drugs, namely, as an activating component of $K^+$ channel activation drugs such as an anti-asthma drug, a hypertension drug, an anti-angina pectoris drug and an incontinence curing drug. The administration dose of the compound represented by the general formula (I) depends upon the kinds and degrees of diseases. Generally, it is about 0.0001 to 1 mg/kg/day, preferably 0.001 to 0.1 mg/kg/day. A route of administration can be selected, as required, from oral administration, parenteral administration, topical administration and the like. As a carrier of a $K^+$ channel activation drug can be used a carrier ordinarily used.

Among the compounds represented by the general formula (I) of the present invention, the compounds having a nitro group at the 4-position of a benzopyran ring including the compound represented by the general formula (II) exhibit excellent $K^+$ channel activation effects (refer to Test Examples):

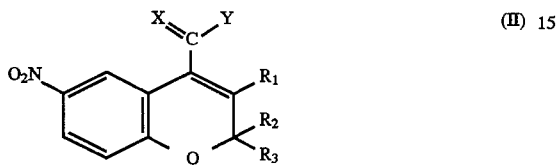

(II)

wherein

X' represents =O, =S or =N—CN, and

Y' represents —$NR_{10}R_{11}$, wherein $R_{10}$ and $R_{11}$ represent, in common with each other or independently, a hydrogen atom, a lower alkyl group or a lower alkyl group substituted by a cyano group; $R_1$, $R_2$ and $R_3$ mean as defined above. Particularly, compounds wherein $R_6$ or $R_7$ ($R_{10}$ or $R_{11}$) is a hydrogen atom have strong activities. As concrete examples of the compounds of the present invention can be mentioned the following:

TABLE 1

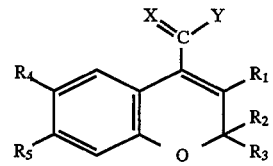

| Ex. No. | $R_1$ | $R_2$ | $R_3$ | $R_4$ | $R_5$ | X | Y |
|---|---|---|---|---|---|---|---|
| 1(1) | OH | Me | $CH_2OMe$ | $NO_2$ | H | S | NHMe |
| 1(2) | H | Me | $CH_2OMe$ | $NO_2$ | H | O | NHMe |
| 2 | H | Me | $CH_2OMe$ | $NO_2$ | H | S | NHMe |
| 3 | H | Me | $CH_2OMe$ | $NO_2$ | H | N—CN | NHMe |
| 4 | H | Me | $CH_2OMe$ | $NO_2$ | H | N—CN | $NMe_2$ |
| 5(1) | OH | $CH_2OMe$ | $CH_2OMe$ | $NO_2$ | H | S | NHMe |
| 5(2) | H | $CH_2OMe$ | $CH_2OMe$ | $NO_2$ | H | O | NHMe |
| 6 | H | $CH_2OMe$ | $CH_2OMe$ | $NO_2$ | H | S | NHMe |
| 7 | H | $CH_2F$ | $CH_2F$ | $NO_2$ | H | O | NHMe |
| 8 | H | $CH_2F$ | $CH_2F$ | $NO_2$ | H | S | NHMe |
| 9 | H | $CH_2F$ | $CH_2F$ | $NO_2$ | H | N—CN | NHMe |
| 10 | H | $CH_2F$ | $CH_2F$ | $NO_2$ | H | O | $NHCH_2CH_2CN$ |
| 11(1) | OH | —$CH_2CH_2OCH_2CH_2$— | | $NO_2$ | H | S | NHMe |
| 11(2) | H | —$CH_2CH_2OCH_2CH_2$— | | $NO_2$ | H | O | NHMe |
| 12 | H | —$CH_2CH_2OCH_2CH_2$— | | $NO_2$ | H | S | NHMe |
| 13 | H | —$CH_2CH_2OCH_2CH_2$— | | $NO_2$ | H | N—CN | NHMe |
| 14 | H | —$CH_2CH_2OCH_2CH_2$— | | $NO_2$ | H | N—CN | $NMe_2$ |
| 15 | H | —$CH_2CH_2SCH_2CH_2$— | | $NO_2$ | H | O | NHMe |
| 16 | H | $CH_2F$ | $CH_2F$ | $NO_2$ | H | S | $NHCH_2CH_2CN$ |
| 17(2) | H | $CH_2F$ | $CH_2F$ | Cl | Cl | O | OH |
| 17(3) | H | $CH_2F$ | $CH_2F$ | Cl | Cl | O | NHMe |
| 18 | H | $CH_2F$ | $CH_2F$ | Cl | Cl | S | NHMe |
| 19 | H | $CH_2F$ | $CH_2F$ | Cl | Cl | O | $NHCH_2CH_2CN$ |
| 20 | H | $CH_2F$ | $CH_2F$ | Cl | Cl | S | $NHCH_2CH_2CN$ |
| 21(3) | H | $CH_2F$ | $CH_2F$ | Br | H | O | OH |
| 21(4) | H | $CH_2F$ | $CH_2F$ | Br | H | O | $NHCH_2CH_2CN$ |
| 22 | H | $CH_2F$ | $CH_2F$ | Br | H | O | NHMe |
| 23(1) | H | $CH_2F$ | $CH_2F$ | $NO_2$ | H | O | OEt |
| 23(2) | H | $CH_2F$ | $CH_2F$ | $NH_2$ | H | O | OEt |
| 23(3) | H | $CH_2F$ | $CH_2F$ | I | H | O | OEt |
| 23(4) | H | $CH_2F$ | $CH_2F$ | $CF_3$ | H | O | OEt |
| 23(5) | H | $CH_2F$ | $CH_2F$ | $CF_3$ | H | O | OH |
| 23(6) | H | $CH_2F$ | $CH_2F$ | $CF_3$ | H | O | NHMe |
| 24 | H | $CH_2F$ | $CH_2F$ | $CF_3$ | H | S | NHMe |
| 25 | H | $CH_2F$ | $CH_2F$ | $CF_3$ | H | O | $NHCH_2CH_2CN$ |
| 26(1) | H | $CH_2F$ | $CH_2F$ | $C_2F_5$ | H | O | OEt |
| 26(2) | H | $CH_2F$ | $CH_2F$ | $C_2F_5$ | H | O | OH |
| 26(3) | H | $CH_2F$ | $CH_2F$ | $C_2F_5$ | H | O | NHMe |
| 27 | H | $CH_2F$ | $CH_2F$ | $C_2F_5$ | H | S | NHMe |
| 28 | H | $CH_2F$ | $CH_2F$ | $C_2F_5$ | H | N—CN | NHMe |

TABLE 1-continued

![structure: benzopyran with X=C-Y at position 4, R1, R2, R3 at 3-position, R4, R5 on aromatic ring]

| Ex. No. | R₁ | R₂ | R₃ | R₄ | R₅ | X | Y |
|---|---|---|---|---|---|---|---|
| 29.41 | H | CH₂F | CH₂F | C₂F₅ | H | O | NHCH₂CH₂CN |
| 30(1) | H | CH₂F | CH₂F | n-C₃F₇ | H | O | OEt |
|  | H | CH₂F | CH₂F | H | H | O | OEt |
| 30(2) | H | CH₂F | CH₂F | n-C₃F₇ | H | O | OH |
| 30(3) | H | CH₂F | CH₂F | n-C₃F₇ | H | O | NHMe |
| 31 | H | CH₂F | CH₂F | n-C₃F₇ | H | S | NHMe |
| 32 | H | CH₂F | CH₂F | n-C₃F₇ | H | O | NHCH₂CH₂CN |
| 33(1) | H | CH₂F | CH₂F | H | H | O | OH |
| 33(2) | H | CH₂F | CH₂F | H | H | O | NHMe |
| 34 | H | CH₂F | CH₂F | H | H | O | NHCH₂CH₂CN |
| 35(1) | H | CH₂F | CH₂F | CN | H | O | OEt |
| 35(2) | H | CH₂F | CH₂F | CN | H | O | OH |
| 35(3) | H | CH₂F | CH₂F | CN | H | O | NHMe |
| 36 | H | CH₂F | CH₂F | CN | H | O | NHCH₂CH₂CN |
| 37 | H | CH₂F | CH₂F | NO₂ | H | O | NHCH₂CH₂CN (3,4-dihydro) |
| 38 | H | CH₂F | CH₂F | NO₂ | H | S | NHCH₂CH₂CN (3,4-dihydro) |
| 39(2) | H | CH₂F | CH₂F | NH₂.HCl | H | O | NHCH₂CH₂CN |
| 40 | H | CH₂F | CH₂F | I | H | O | NHCH₂CH₂CN |
| 42(3) | H | CH₂F | Me | NO₂ | H | O | OH |
| 42(4) | H | CH₂F | Me | NO₂ | H | O | NHMe |
| 43 | H | CH₂F | Me | NO₂ | H | S | NHMe |
| 44 | H | CH₂F | Me | NO₂ | H | O | NHCH₂CH₂CN |
| 45 | H | CH₂F | Me | NO₂ | H | S | NHCH₂CH₂CN |
| 46(3) | H | CF₃ | Me | NO₂ | H | O | OH |
| 46(4) | H | CF₃ | Me | NO₂ | H | O | NHMe |
| 47 | H | CF₃ | Me | NO₂ | H | S | NHMe |
| 48 | H | CF₃ | Me | NO₂ | H | O | NHCH₂CH₂CN |
| 49 | H | CF₃ | Me | NO₂ | H | S | NHCH₂CH₂CN |
| 50(1) | H | CH₂F | CH₂F | n-C₄F₉ | H | O | OEt |
| 50(2) | H | CH₂F | CH₂F | n-C₄F₉ | H | O | OH |
| 50(3) | H | CH₂F | CH₂F | n-C₄F₉ | H | O | NHMe |
| 51 | H | CH₂F | CH₂F | n-C₄F₉ | H | O | NHCH₂CH₂CN |
| 52(1) | H | CH₂F | CH₂F | Cl | H | O | OEt |
| 52(2) | H | CH₂F | CH₂F | Cl | H | O | OH |
| 52(3) | H | CH₂F | CH₂F | Cl | H | O | NHMe |
| 53 | H | CH₂F | CH₂F | Cl | H | O | NHCH₂CH₂CN |

Hereinafter, the production of the compound of the present invention will be explained more minutely according to Examples. The present invention is not restricted to these Examples, though.

Example 1

2-Methoxymethyl-N,2-dimethyl-6-nitro-2H-1-benzopyran-4-carboxamide

(1) To a mixture of 5 g of 3,4-dihydro-2-methoxymethyl-2-methyl-6-nitro-2H-1-benzopyran-3-one and 60 ml of dried N,N-dimethylformamide was added 2.5 g of potassium tertiary butoxide under nitrogen stream with stirring under ice-cooling and the mixture was stirred for 5 minutes. Then, 1.7 ml of methyl isothiocyanate in 3 ml of N,N-dimethylformamide was added to the mixture and it was stirred at 5° C. for 18 hours. Ice water was added to the mixture and it was washed with ether. A water layer was acidified to be hydrochloric acid and extracted with ether. After an organic layer was washed with water and dried, the solvent was distilled. The resultant residue was purified according to silica gel column chromatography (developing solution, hexane:AcOEt=3:1) to obtain 5.1 g of 3-hydroxy-2-methoxymethyl-N,2-dimethyl-6-nitro-2H-1-benzopyran-4-carbothioamide with a melting point of 139°–141° C.

NMR (CDCl₃)δ: 1.40(3H,s), 3.28(3H,d), 3.31(3H,s), 3.65 (2H,s), 6.98(1H,d), 7.95(1H,dd), 7.98(1H,d).

MS m/z: 324 (M⁺)

(2) To a mixture of 5.1 g of 3-hydroxy-2-methoxymethyl-N,2-dimethyl-6-nitro-2H-1-benzopyran-4-carbothioamide, 75 ml of tetrahydrofuran and 125 ml of methanol was added 3.0 g of sodium borohydride (NaBH₄). The mixture was stirred under ice-cooling for 2 hours and subsequently stirred at room temperature for 24 hours. The reaction solution was vacuum-distilled and water was added to it and the resultant solution was extracted with methylene chloride. After an organic layer was washed with water and dried, the solvent was distilled to obtain 2 g of N-methyl-3,4-dihydro-3-hydroxy-2-methoxymethyl-2-methyl-6-nitro-2H-1-benzopyran-4-carbothioamide. Subsequently, to 1 g of the obtained benzopyran derivative were added 1.17 g of p-toluenesulfonyl chloride and 25 ml of pyridine. The resultant mixture was refluxed with heating for 1 hour and the solvent was distilled. Ice water was added to the residue and it was acidified to be hydrochloric acid and extracted with methylene chloride. An organic layer was washed with water and dried, and the solvent was distilled. The resultant residue was purified according to silica gel column chromatography (developing solution, hexane:AcOEt=1:1) to obtain 680 mg of 2-methoxymethyl-N,2-dimethyl-6-nitro-2H-1-benzopyran-4-carboxamide with a melting point of 128°–130° C.

NMR (CDCl$_3$)δ: 1.40(3H,s), 2.88(3H,d), 3.30(3H,s), 3.49 (2H,s), 6.06(1H,s), 6.81(1H,d), 7.18(1H,brs), 7.91(1H, dd), 8.38(1H,d).

MS m/z: 292 (M$^+$)

Example 2

2-Methoxymethyl-N,2-dimethyl-6-nitro-2H-1-benzopyran-4-carbothioamide

A mixture of 0.9 g of 3,4-dihydro-3-hydroxy-2-methoxymethyl-N,2-dimethyl-6-nitro-2H-1-benzopyran-4-carbothioamide, 0.12 g of p-toluenesulfonic acid monohydrate and 25 ml of toluene was refluxed with heating for 2 hours. Ethyl acetate was added to the mixture. After it was washed with water and dried, the solvent was distilled. The resultant residue was purified according to silica gel column chromatography (developing solution. MeOH:CH$_2$Cl$_2$=1:99) to obtain 600 mg of 2-methoxymethyl-N,2-dimethyl-6-nitro-2H-1-benzopyran-4-carbothioamide with a melting point of 146°–148° C.

NMR (CDCl$_3$)δ: 1.47(3H,s), 3.23(3H,d), 3.31(3H,s), 3.49 (2H,s), 5.80(1H,s), 6.78(1H,d), 7.92(1H,dd), 7.93(1H, brs), 8.25(1H,d).

MS m/z: 308 (M$^+$)

Example 3

N-Cyano-2-methoxymethyl-N',2-dimethyl-6-nitro-2H-1-benzopyran-4-amidine

A mixture of 158 mg of 2-methoxymethyl-N,2-dimethyl-6-nitro-2H-1-benzopyran-4-carbothioamide, 157 mg of 2-chloro-1-methylpyridinium iodide, 172 μl of triethylamine and 4 ml of dried tetrahydrofuran was refluxed with heating for 3 hours. The mixture was cooled to room temperature and to the resultant mixture were added 34 mg of cyanamide and 25 mg sodium hydride (60%) and the mixture was refluxed with heating for 4 hours. Ice water was added to the reaction product and it was extracted with ethyl acetate. An organic layer was washed with water and dried, and the solvent was distilled. The resultant residue was purified according to silica gel column chromatography (developing solution, MeOH:CH$_2$Cl$_2$=1:99) to obtain 20 mg of N-cyano-2-methoxymethyl-N',2-dimethyl-6-nitro-2H-1-benzopyran-4-amidine with a melting point of 121°–125° C. by recrystallization from ethyl acetate.

NMR (CDCl$_3$)δ: 1.28(3H,s), 3.02(3H,d), 3.40(3H,s), 3.58 (2H,s), 6.01(1H,s), 6.90(1H,d), 7.51(1H,brs), 7.88(1H,d), 8.01(1H,dd).

MS m/z: 316 (M$^+$)

Example 4

N-Cyano-2-methoxymethyl-N',N',2-trimethyl-6-nitro-2H-1-benzopyran-4-amidine To a mixture of 130 mg of 2-methoxymethyl-N,2-dimethyl-6-nitro-2H-1-benzopyran-4-carboxamide, 83 μl of methyl iodide and 5 ml of dried N,N-dimethylformamide was added 21 mg of sodium hydride (60%) with stirring under ice-cooling and stirred at room temperature for 15 hours. Ice water was added to the reaction solution and it was extracted with ether. An organic layer was washed with water and dried, and the solvent was distilled. The resultant residue was purified according to silica gel column chromatography (developing solution, MeOH:CH$_2$Cl$_2$=1:99) to obtain 130 mg of 2-methoxymethyl-N,N,2-trimethyl-6-nitro-2H-1-benzopyran-4-carboxamide. Subsequently, 103 mg of a Lawesson's reagent and 8 ml of benzene were added therein and the resultant mixture was refluxed with heating for 1 hour. After the reaction solution was vacuum-condensed, the residue was purified according to silica gel column chromatography (developing solution, hexane:AcOEt=3:1) to obtain 140 mg of 2-methoxymethyl-N,N,2-trimethyl-6-nitro-2H-1-benzopyran-4-carbothioamide. Subsequently, 290 μl of iodomethane, 104 mg of cyanamide and 8 ml of dried tetrahydrofuran were added therein and 96 mg of sodium hydride (60%) was added therein with stirring under ice-cooling, and the resultant mixture was stirred at room temperature for 15 hours. Ice water was added to the reaction product and it was extracted with ethyl acetate. an organic layer was washed with water and dried, and the solvent was distilled. The resultant residue was purified according to silica gel column chromatography (developing solution, hexane:AcOEt=2:3) to obtain 125 mg of N-cyano-2-methoxymethyl-N',N',2-trimethyl-6-nitro-2H-1-benzopyran-4-amidine with a melting point of 143°–146° C.

NMR (CDCl$_3$)δ: 1.51(3H,s), 3.03(3H,s), 3.21(3H,s), 3.32 (3H,s), 3.54(2H,brs), 5.88(1H,s), 6.85(1H,d), 7.55(1H,d), 8.02(1H,dd).

MS m/z: 330 (M$^+$)

Example 5

2,2-Bis(methoxymethyl)-N-methyl-6-nitro-2H-1-benzopyran-4-carboxamide (1) To a mixture of 5.1 g of 3,4-dihydro-2,2-bis (methoxymethyl)-6-nitro-2H-1-benzopyran-3-one and 60 ml of dried N,N-dimethylformamide was added 1.35 ml of methyl isothiocyanate under nitrogen stream with stirring under ice-cooling. Subsequently, 2.2 g of potassium tertiary butoxide was added therein. The mixture was stirred for 15 minutes and then further stirred at 5° C. for 11 hours. Ice water was added therein and the resultant reaction solution was washed with ether. A water layer was acidified to be hydrochloric acid and it was extracted with ether. An organic layer was washed with water and dried, and the solvent was distilled. The obtained residue was purified according to silica gel column chromatography (developing solution, MeOH:CH$_2$Cl$_2$=2:98) to obtain 2.8 g of 3-hydroxy-2,2-bis (methoxymethyl)-N-methyl-6-nitro-2H-1-benzopyran-4-carbothioamide with a melting point of 97°–101° C.

NMR (CDCl$_3$)δ: 3.28(3H,d), 3.35(6H,s), 3.70(4H,s), 6.98 (1H,d), 7.43(1H,dd), 8.04(1H,d).

MS m/s: 354 (M$^+$)

(2) To a mixture of 2.7 g of 3-hydroxy-2,2-bis (methoxymethyl)-N-methyl-6-nitro-2H-1-benzopyran-4-carbothioamide, 12 ml of tetrahydrofuran and 46 ml of methanol was added 1.1 g of sodium borohydride (NaBH$_4$) with stirring under ice-cooling and stirred under ice-cooling for 2 hours and subsequently further stirred at room temperature for 24 hours. The reaction solution was vacuum-distilled, water was added therein and the resultant mixture was extracted with methylene chloride. An organic layer was washed with water and dried. The solvent was distilled to obtain 1.0 g of 3,4-dihydro-3-hydroxy-2,2-bis (methoxymethyl)-N-methyl-6-nitro-2H-1-benzopyran-4-carbothioamide. Subsequently, to 700 mg of the obtained benzopyran derivative were added 0.75 g of p-toluenesulfonyl chloride and 11 ml of pyridine. The resultant mixture was refluxed with heating for 30 minutes and the solvent was distilled. Ice water was added to the residue and it was acidified to be hydrochloric acid and extracted with methylene chloride. An organic layer was washed with water and dried and the solvent was distilled. The resultant residue was purified according to silica gel column chromatography (developing solution, MeOH:$CH_2Cl_2$=5:95) to obtain 500 mg of 2,2-bis(methoxymethyl)-N-methyl-6-nitro-2H-1-benzopyran-4-carboxamide with a melting point of 147°–149° C.
NMR (CDCl$_3$)δ: 2.94(3H,d), 3.37(6H,s), 3.60(4H,s), 6.08 (1H,s), 6.35(1H,brs), 6.88(1H,d), 8.01(1H,dd), 8.48(1H, d).
MS m/z: 322 (M$^+$)

Example 6

2,2-Bis(methoxymethyl)-N-methyl-6-nitro-2H-1-benzopyran-4-carbothioamide

A mixture of 550 mg of 3,4-dihydro-3-hydroxy-2,2-bis (methoxymethyl)-N-methyl-6-nitro-2H-1-benzopyran-4-carbothioamide, 0.16 g of p-toluenesulfonic acid monohydrate and 8 ml of toluene was refluxed with heating for 1.5 hours. Toluene was added to the mixture. After it was washed with water and dried, the solvent was distilled. The resultant residue was purified according to silica gel column chromatography (developing solution, MeOH:$CH_2Cl_2$= 1:99) to obtain 110 mg of oily 2,2-bis(methoxymethyl)-N-methyl-6-nitro-2H-1-benzopyran-4-carbothioamide.
NMR (CDCl$_3$)δ: 3.25(3H,d), 3.35(6H,s), 3.58(4H,s), 5.82 (1H,s), 6.85(1H,d), 7.97(1H,dd), 8.02(1H,brs), 8.34(1H, d).
MS m/z: 338 (M$^+$)

Example 7

2,2-Bis(fluoromethyl)-N-methyl-6-nitro-2H-1-benzopyran-4-carboxamide (1) To a mixture of 4.05 g of 2,2-bis(fluoromethyl)-3,4-dihydro-6-nitro-2H-1-benzopyran-4-one and 10 ml of dried benzene was added 2.52 ml of trimethylsilyl cyanide with stirring under ice-cooling. 0.82 g of zinc iodide was added therein and the mixture was stirred at room temperature for 12 hours. Further, 8 ml of pyridine and 4.41 ml of phosphorus oxychloride were added therein and the resultant mixture was refluxed with heating for 6 hours. Ice water was added to the residue and it was acidified to be hydrochloric acid and it was extracted with methylene chloride. An organic layer was washed with water and dried, and the solvent was distilled. The obtained residue was purified according to silica gel column chromatography (developing solution, $CH_2Cl_2$:hexane=7:3) to obtain 0.99 g of 4-cyano-2,2-bis(fluoromethyl)-6-nitro-2H-1-benzopyran with a melting point of 136°–137° C.
NMR (CDCl$_3$)δ: 4.57(4H,d), 6.50(1H,s), 6.97(2H,dd), 8.14 (2H,dd), 8.23(1H,s).
MS m/z: 266 (M$^+$)

(2) A mixture of 0.93 g of 4-cyano-2,2-bis(fluoromethyl) -6-nitro-2H-1-benzopyran, 20 ml of acetic acid, 10 ml of water and 10 ml of concentrated sulfuric acid was refluxed with heating for 4.5 hours. When the reaction mixture was poured into ice water, crystals were separated out. Said crystals were dissolved with a sodium hydrogen carbonate solution and washed with methylene chloride. A water layer was acidified to be hydrochloric acid and extracted with methylene chloride. An organic layer was washed with water and dried, and the solvent was distilled to obtain 0.83 g of 2,2-bis(fluoromethyl)-6-nitro-2H-1-benzopyran-4-carboxylic acid with a melting point of 171°–172° C.
IR (KBr) cm$^{-1}$: 1698 (C=O)
MS m/z: 285 (M$^+$)

(3) To a mixture of 0.78 g of 2,2-bis(fluoromethyl)-6-nitro-2H-1-benzopyran-4-carboxylic acid and 5 ml of tetrahydrofuran was added 0.67 g of 1,1'-carbonyldiimidazole with stirring under ice-cooling and the mixture was stirred for 1 hour. Then, 6.3 ml of 40% methylamine (methanol solution) was added therein. The resultant mixture was stirred under ice-cooling for 1 hour and then at room temperature for 14 hours. An aqueous potassium carbonate solution was added therein and the mixture was extracted with ether. An organic layer was washed with water and dried, and the solvent was distilled. The obtained residue was purified according to silica gel column chromatography (developing solution, MeOH:$CH_2Cl_2$=1:99) to obtain 0.13 g of 2,2-bis(fluoromethyl)-N-methyl-6-nitro-2H-1-benzopyran-4-carboxamide with a melting point of 178°–179° C.
NMR (CDCl$_3$)δ: 2.80(3H,d), 4.68(4H,d), 6.21(1H,s), 7.08 (1H,d), 8.10(1H,dd), 8.46(1H,brs), 8.48(1H,d).
MS m/z: 298 (M$^+$)

Example 8

2,2-Bis(fluoromethyl)-N-methyl-6-nitro-2H-1-benzopyran-4-carbothioamide (1) A mixture of 0.08 g of 2,2-bis(fluoromethyl)-N-methyl-6-nitro-2H-1-benzopyran-4-carboxamide, 0.06 g of a Lawesson's reagent and 2 ml of benzene was refluxed with heating for 1 hour. The solvent was distilled. The resultant residue was purified according to silica gel column chromatography (developing solution:$CH_2Cl_2$) and further recrystallized by a mixed solvent of ethyl acetate and hexane to obtain 71 mg of 2,2-bis(fluoromethyl)-N-methyl-6-nitro-2H-1-benzopyran-4-carbothioamide with a melting point of 134°–135° C.
NMR (CDCl$_3$)δ: 3.30(3H,d), 4.60(4H,d), 5.85(1H,s), 6.98 (1H,d), 7.97(1H,brs), 8.07(1H,dd), 8.37(1H,d).
MS m/z: 314 (M$^+$)

Example 9

N-Cyano-2,2-bis(fluoromethyl)-N'-methyl-6-nitro-2H-1-benzopyran-4-amidine

A mixture of 84 mg of 2,2-bis(fluoromethyl)-N-methyl-6-nitro-2H-1-benzopyran-4-carbothioamide, 140 mg of 2-chloro-1-methylpyridinium iodide, 0.06 ml of triethylamine and 2 ml of dried tetrahydrofuran was refluxed with heating for 2 hours. After the reaction solution was cooled to room temperature, 42 mg of cyanamide and 38 mg of sodium hydride (60%) were added therein and the resultant mixture was refluxed with heating for 4 hours. Ice water was added therein and the mixture was extracted with methylene chloride. An organic layer was washed with water and dried, and the solvent was distilled. The obtained residue was purified according to silica gel column chromatography (developing solution, MeOH:$CH_2Cl_2$=1:99). The resultant product was recrystallized by a mixed solvent of ethyl acetate and hexane to obtain 21.5 mg of N-cyano-2,2-bis (fluoromethyl)-N'-methyl-6-nitro-2H-1-benzopyran-4-amidine with a melting point of 259°–261° C.
NMR (CDCl$_3$-DMSO-d$_6$)δ: 2.96(3H,d), 4.77(4H,d), 6.20 (1H,s), 7.17(1H,d), 7.81(1H,d), 8.12(1H,dd).
MS m/z: 322 (M$^+$)

Example 10

N-(2-Cyanoethyl)-2,2-bis(fluoromethyl)-6-nitro-2H-1-benzopyran-4-carboxamide To a mixture of 30 mg of 2,2-bis(fluoromethyl)-6-nitro-2H-1-benzopyran-4-carboxylic acid and 2 ml of tetrahydrofuran was added 28 mg of 1,1'-carbonyldiimidazole with stirring under ice-cooling and the mixture was stirred for 1 hour. Then, 0.10 ml of 2-cyanoethylamine was added therein, and the resultant mixture was stirred under ice-cooling for 1 hour and subsequently at room temperature for 12 hours. An aqueous potassium carbonate solution was added therein and the reaction solution was extracted with methylene chloride. An organic layer was washed with water and dried, and the solvent was distilled. The resultant residue was recrystallized by a mixed solvent of ethyl acetate and hexane to obtain 26.6 mg of N-(2-cyanoethyl)-2,2-bis(fluoromethyl)-6-nitro-2H-1-benzopyran-4-carboxamide with a melting point of 173°–174° C.

NMR ($CDCl_3$—$CF_3COOD$)δ: 2.89(2H,t), 3.81(2H,t), 4.61 (4H,d), 6.24(1H,s), 7.05(1H,d), 8.15(1H,dd), 8.29(1H,d).
MS m/z: 337 ($M^+$)

Example 11

N-Methyl-6-nitrospiro[2H-1-benzopyran-2,4'-tetrahydropyran]-4-carboxamide (1) To a mixture of 4.8 g of 3,4-dihydro-6-nitrospiro[2H-1-benzopyran-2,4'-tetrahydropyran]-3-one and 60 ml of dried N,N-dimethylformamide was added 1.65 g of methyl isothiocyanate under nitrogen stream. Then, 2.39 g of potassium tertiary butoxide was added therein with stirring under ice-cooling and the mixture was stirred for 1 hour and then stirred at 5° C. for 17 hours. Ice water was added to the reaction solution and it was washed with ether. A water layer was acidified to be hydrochloric acid and extracted with ether. An organic layer was washed with water and dried, and the solvent was distilled. The obtained residue was recrystallized by a mixed solvent of ethyl acetate and hexane to obtain 3.8 g of 3-hydroxy-N-methyl-6-nitrospiro-[2H-1-benzopyran-2,4'-tetrahydropyran]-4-carbothioamide with a melting point of 217°–218° C.

NMR ($CDCl_3$-$DMSO$-$d_6$)δ: 1.47–2.50(4H,m), 3.17(3H, brs), 3.81(4H,dd), 7.07(1H,dd), 7.96(1H,dd), 8.03(1H, brs), 9.70(1H,brs).
MS m/z: 336 ($M^+$)

(2) To a mixture of 3.7 g of 3-hydroxy-N-methyl-6-nitrospiro[2H-1-benzopyran-2,4'-tetrahydropyran]-4-carbothioamide, 100 ml of tetrahydrofuran and 100 ml of methanol was added 2.8 g of sodium borohydride ($NaBH_4$) with stirring under ice-cooling, and the mixture was stirred under ice-cooling for 30 minutes and then at room temperature for 24 hours. The reaction solution was vacuum-distilled, water was added therein and the resultant mixture was extracted with methylene chloride. An organic layer was washed with water and dried. The solvent was distilled to obtain 1.7 g of 3,4-dihydro-3-hydroxy-N-methyl-6-nitrospiro[2H-1-benzopyran-2,4'-tetrahydropyran]-4-carbothioamide. Subsequently, to 1.5 g of it were added 2.1 g of p-toluenesulfonyl chloride and 60 ml of pyridine. After the mixture was refluxed with heating for 1 hour, the solvent was distilled. Ice water was added to the residue and the reaction solution was acidified to be hydrochloric acid and extracted with methylene chloride. An organic layer was washed with water and dried, and the solvent was distilled. The residue was purified according to silica gel column chromatography (developing solution, $MeOH$:$CH_2Cl_2$= 1:99) to obtain 1.2 g of N-methyl-6-nitrospiro[2H-1-benzopyran-2,4'-tetrahydropyran]-4-carboxamide with a melting point of 183°–184° C.

NMR ($CDCl_3$)δ: 1.55–2.10(4H,m), 2.90(3H,d), 3.80(4H, dd), 6.00(1H,s), 6.50(1H,brd), 6.89(1H,d), 7.97(1H,dd), 8.37(1H,d).
MS m/z: 304 ($M^+$)

Example 12

N-Methyl-6-nitrospiro[2H-1-benzopyran-2,4'-tetrahydropyran]-4-carbothioamide A mixture of 1.66 g of 3,4-dihydro-3-hydroxy-N-methyl-6-nitrospiro[2H-1-benzopyran-2,4'-tetrahydropyran]-4-carbothioamide, 1.0 g of p-toluenesulfonic acid monohydrate and 100 ml of toluene was refluxed with heating for 1.5 hours. Water was added therein and the mixture was extracted with methylene chloride. An organic layer was washed and dried, and the solvent was distilled. The obtained residue was purified according to silica gel column chromatography (developing solution, $MeOH$:$CH_2Cl_2$= 1:99) to obtain 0.93 g of N-methyl-6-nitrospiro[2H-1-benzopyran-2,4'-tetrahydropyran]-4-carbothioamide with a melting point of 223°–225° C.

NMR ($CDCl_6$-$DMSO$-$d_6$)δ: 1.75–2.10(4H,m), 3.22(3H,d), 3.83(4H,dd), 5.83(1H,s), 6.95(1H,d), 8.02(1H,dd), 8.36 (1H,d), 9.65(1H,brs).
MS m/z: 320 ($M^+$)

Example 13

N-Cyano-N'-methyl-6-nitrospiro[2H-1-benzopyran-2,4'-tetrahydropyran]-4-amidine A mixture of 200 mg of N-methyl-6-nitrospiro[2H-1-benzopyran-2,4'-tetrahydropyran]-4-carbothioamide, 192 mg of 2-chloro-1-methylpyridinium iodide, 209 μl of triethylamine and 5 ml of dried tetrahydrofuran was refluxed with heating for 2 hours and further cooled to room temperature. 42 mg of cyanamide and 30 mg of sodium hydride (60%) were added therein and the reaction mixture was refluxed with heating for 2 hours. Ice water was added therein and the resultant mixture was extracted with methylene chloride. An organic layer was washed with water and dried, and the solvent was distilled. The obtained residue was purified according to silica gel column chromatography (developing solution, $CH_2Cl_2$) and recrystallized by a mixed solvent of ethyl acetate and hexane to obtain 14 mg of N-cyano-N'-methyl-6-nitrospiro[2H-1-benzopyran-2,4'-tetrahydropyran]-4-amidine with a melting point of 293°–294° C.

NMR ($CDCl_3$-$CD_3OD$)δ: 1.80–2.10(4H,m), 3.10(3H,s), 3.70–4.00(4H,m), 6.02(1H,s), 7.02(1H,d), 7.90(1H,d), 8.15(1H,dd).
MS m/z: 328 ($M^+$)

Example 14

N-Cyano-N',N'-dimethyl-6-nitrospiro[2H-1-benzopyran-2,4'-tetrahydropyran]-4-amidine To a mixture of 0.64 g of N-methyl-6-nitrospiro[2H-1-benzopyran-2,4'-tetrahydropyran]-4-carboxamide, 1.05 g of methyl iodide and 40 ml of dried N,N-dimethylformamide was added 0.13 g of sodium hydride (60%) with stirring under ice-cooling and the mixture was stirred at room temperature for 17 hours. Ice water was added therein and the resultant mixture was extracted with ether. An organic layer was washed with water and dried. The solvent was distilled to obtain 0.65 g of N,N-dimethyl-6-nitrospiro[2H-1-benzopyran-2,4'-tetrahydropyran]-4-carboxamide. Subsequently, 0.63 g of a Lawesson's reagent and 30 ml of benzene were added therein, and the mixture was refluxed with heating for 1.5 hours. After the reaction solution was vacuum-condensed, the residue was purified according to silica gel column chromatography (developing solution, MeOH:CH$_2$Cl$_2$=1:99) to obtain 0.43 g of N,N-dimethyl-6-nitrospiro[2H-1-benzopyran-2,4'-tetrahydropyran]-4-carbothioamide. Subsequently, 1.80 g of methyl iodide, 0.28 g of cyanamide and 20 ml of tetrahydrofuran were added therein. 0.29 g of sodium hydride (60%) was added therein with stirring under ice-cooling and the mixture was stirred at room temperature for 17 hours. Ice water was added therein and the resultant mixture was extracted with methylene chloride. After an organic layer was washed with water and dried, the solvent was distilled. The resultant residue was purified according to silica gel column chromatography (developing solution, MeOH:CH$_2$Cl$_2$=1:99) to obtain 0.28 g of N-cyano-N',N'-dimethyl-6-nitrospiro[2H-1-benzopyran-2,4'-tetrahydro-pyran]-4-amidine with a melting point of 202°–203° C.

NMR (CDCl$_3$)δ: 1.80–2.21(4H,m), 3.01(3H,s), 3.24(3H,s), 3.55–4.10(4H,m), 5.94(1H,s), 7.01(1H,d), 7.65(1H,d), 8.06(1H,dd).

MS m/z: 342 (M$^+$)

Example 15

N-Methyl-6-nitrospiro[2H-1-benzopyran-2,4'-tetrahydrothiopyran]-4-carboxamide (1) To a mixture of 3.08 g of 3,4-dihydro-6-nitrospiro[2H-1-benzopyran-2,4'-tetrahydrothiopyran]-4-one and 40 ml of dried benzene was added 1.8 ml of trimethylsilyl cyanide with stirring under ice-cooling. 1.22 g of zinc iodide was added therein and the resultant mixture was stirred at room temperature for 19 hours. 6 ml of pyridine and 3.1 ml of phosphorus oxychloride were added therein and the mixture was refluxed with heating for 5.5 hours. Ice water was added to the residue, and the residue was acidified to be hydrochloric acid and extracted with methylene chloride. An organic layer was washed with water and dried, and the solvent was distilled. The resultant residue was purified according to silica gel column chromatography (developing solution: CH$_2$Cl$_2$) to obtain 0.28 g of 6-nitrospiro[2H-1-benzopyran-2,4'-tetrahydrothiopyran]-4-carbonitrile with a melting point of 175°–176° C.

NMR (CDCl$_3$)δ: 1.60–3.40(8H,m), 6.42(1H,s), 6.96(1H,d), 8.11(1H,dd), 8.20(1H,s).

MS m/z: 288 (M$^+$)

(2) A mixture of 0.13 g of 6-nitrospiro[2H-1-benzopyran-2,4'-tetrahydrothiopyran]-4-carbonitrile, 10 ml of acetic acid, 5 ml of water and 5 ml of concentrated sulfuric acid was refluxed with heating for 2 hours. When the reaction mixture was poured into ice water, crystals were separated out. The crystals were dissolved into a sodium hydrogen-carbonate solution and washed with methylene chloride. A water layer was acidified to be hydrochloric acid and extracted with methylene chloride. After an organic layer was washed with water and dried, the solvent was distilled. The resultant residue was crystallized by a mixed solvent of ethyl acetate and methanol to obtain 55 mg of 6-nitrospiro[2H-1-benzopyran-2,4'-tetrahydrothiopyran]-4-carboxylic acid with a melting point of 259°–261° C.

IR (KBr) cm$^{-1}$: 1696 (C=O)

MS m/z : 307 (M$^+$)

(3) To a mixture of 80 mg of 6-nitrospiro[2H-1-benzopyran-2,4'-tetrahydrothiopyran]-4-carboxylic acid and 7 ml of tetrahydrofuran was added 80 mg of 1,1'-carbonyldiimidazole with stirring under ice-cooling and the mixture was stirred for 1 hour. 0.7 ml of 40% methylamine (methanol solution) was added therein and the mixture was stirred under ice-cooling for 1 hour and then at room temperature for 20 hours. An aqueous potassium carbonate solution was added therein and the reaction mixture was extracted with methylene chloride. An organic layer was washed with water and dried, and the solvent was distilled. The residue was purified according to silica gel column chromatography (developing solution, MeOH:CH$_2$Cl$_2$=1:99) and further recrystallized by a mixed solvent of ethyl acetate and hexane to obtain 28 mg of N-methyl-6-nitrospiro[2H-1-benzopyran-2,4'-tetrahydrothiopyran]-4-carboxamide with a melting point of 208°–209° C.

NMR (CDCl$_3$)δ: 1.62–3.34(8H,m), 2.94(3H,d), 5.98(1H,s), 6.22(1H,brs), 6.94(1H,d), 8.09(1H,dd), 8.44(1H,d).

MS m/z: 320 (M$^+$)

Example 16

N-(2-Cyanoethyl)-2,2-bis(fluoromethyl)-6-nitro-2H-1-benzopyran-4-carbothioamide

A mixture of 0.11 g of N-(2-cyanoethyl)-2,2-bis(fluoromethyl)-6-nitro-2H-1-benzopyran-4-carboxamide and 0.17 g of a Lawesson's reagent and 10 ml of benzene was refluxed with heating for 2 hours. The solvent was distilled and the obtained residue was purified according to silica gel column chromatography (developing solution, MeOH:CH$_2$Cl$_2$=1:99) and further recrystallyzed by a mixed solvent of ethyl acetate and hexane to obtain 42 mg of N-(2-cyanoethyl)-2,2-bis(fluoromethyl)-6-nitro-2H-1-benzopyran-4-carbothioamide with a melting point of 114°–116° C.

NMR (CDCl$_3$)δ: 2.91(2H,t), 4.02(2H,dt), 4.56(2H,d), 4.59 (2H,d), 5.86(1H,s), 6.95(1H,d), 8.04(1H,dd), 8.32(1H,d), 8.37(1H,brs).

MS m/z: 353 (M$^+$)

Example 17

6,7-Dichloro-2,2-bis(fluoromethyl)-N-methyl-2H-1-benzopyran-4-carboxamide (1) Using 6,7-dichloro-2,2-bis(fluoromethyl)-3,4-dihydro-2H-1-benzopyran-4-one as a starting material, 6,7-dichloro-4-cyano-2,2-bis(fluoromethyl)-2H-1-benzopyran with a melting point of 98°–99° C. was obtained according to the same method as in Example 7 (1).

NMR (CDCl$_3$)δ: 4.49(2H,d), 4.50(2H,d), 6.36(1H,s), 6.95 (1H,s), 7.35(1H,s).

MS m/z: 289 (M$^+$)

(2) Using 6,7-dichloro-4-cyano-2,2-bis(fluoromethyl)-2H-1-benzopyran, 6,7-dichloro-2,2-bis(fluoromethyl)-2H-1-benzopyran-4-carboxylic acid with a melting point of 192°–193° C. was obtained according to the same method as in Example 7 (2).

NMR (CDCl$_3$-CD$_3$OD)δ: 4.50(2H,d), 4.54(2H,d), 6.67(1H, s), 6.97(1H,s), 8.15(1H,s).

MS m/z: 308 (M$^+$)

(3) Using 6,7-dichloro-2,2-bis(fluoromethyl)-2H-1-benzopyran-4-carboxylic acid, 6,7-dichloro-2,2-bis(fluoromethyl)-N-methyl-2H-1-benzopyran-4-carboxamide with a melting point of 141°–142° C. was obtained according to the same method as In Example 7 (3).

NMR (CDCl$_3$)δ: 2.87(3H,d), 4.45(2H,d), 4.48(2H,d), 5.88 (1H,s), 6.26(1H,brs), 6.91(1H,s), 7.55(1H,s).

MS m/z : 321 (M$^+$)

Example 18

6,7-Dichloro-2,2-bis(fluoromethyl)-N-methyl-2H-1-benzopyran-4-carbothioamide

Using 6,7-dichloro-2,2-bis(fluoromethyl)-N-methyl-2H-1-benzopyran-4-carboxamide, 6,7-dichloro-2,2-bis(fluoromethyl)-N-methyl-2H-1-benzopyran-4-carbothioamide with a melting point of 142°–143° C. was obtained according to the same method as in Example 8.

NMR (CDCl$_3$)δ: 3.22(3H,d), 4.49(2H,d), 4.52(2H,d), 5.74 (1H,s), 6.96(1H,s), 7.46(1H,s), 7.67(1H,brs).
MS m/z: 337 (M$^+$)

Example 19

6,7-Dichloro-N-(2-cyanoethyl)-2,2-bis(fluoromethyl)-2H-1-benzopyran-4-carboxamide A mixture of 0.09 g of 6,7-dichloro-2,2-bis(fluoromethyl)-2H-1-benzopyran-4-carboxylic acid and 3 ml of thionyl chloride was refluxed with heating for 3 hours. The solvent was distilled. The obtained residue was dissolved into 5 ml of methylene chloride. The resultant solution was dropped into a mixed solution of 0.07 g of 2-cyanoethylamine, 0.10 g of triethylamine and 2 ml of methylene chloride under ice-cooling. Subsequently, the reaction solution was stirred at room temperature for 1.5 hours. The solution was acidified to be hydrochloric acid and extracted with a mixed solvent of methanol-methylene chloride. An organic layer was washed with water and dried, and the solvent was distilled. The obtained residue was purified according to silica gel column chromatography (developing solution, MeOH:CH$_2$Cl$_2$=1:99) to obtain 0.09 g of 6,7-dichloro-N-(2-cyanoethyl)-2,2-bis(fluoromethyl)-2H-1-benzopyran-4-carboxamide with a melting point of 135°–136° C.

NMR (CDCl$_3$)δ: 2.68(2H,t), 3.59(2H,dt), 4.48(2H,d), 4.51 (2H,d), 5.99(1H,s), 6.70–7.08(1H,m), 6.97(1H,s), 7.61 (1H,s).
MS m/z: 360 (M$^+$)

Example 20

6,7-Dichloro-N-(2-cyanoethyl)-2,2-bis(fluoromethyl)-2H-1-benzopyran-4-carbothioamide Using 6,7-dichloro-N-(2-cyanoethyl)-2,2-bis(fluoromethyl)-2H-1-benzopyran-4-carboxamide, 6,7-dichloro-N-(2-cyanoethyl)-2,2-bis(fluoromethyl)-2H-1-benzopyran-4-carbothioamide with a melting point of 154°–155° C. was obtained according to the same method as in Example 16.

NMR (CDCl$_3$)δ: 2.87(2H,t), 3.97(2H,dt), 4.49(2H,d), 4.52 (2H,d), 5.77(1H,s), 6.98(1H,s), 7.45(1H,s), 8.25(1H,brs).
MS m/z: 376 (M$^+$)

Example 21

6-Bromo-N-(2-cyanoethyl)-2,2-bis(fluoromethyl)-2H-1-benzopyran-4-carboxamide (1) A mixture of 4.2 g of 4-cyano-2,2-bis(fluoro-methyl)-6-nitro-2H-1-benzopyran, 9.6 g of stannous chloride and 140 ml of ethyl alcohol was stirred with heating at 80° C. for 2 hours. After the mixture was cooled, an aqueous 2N sodium hydroxide solution was added therein to make it alkaline and the resultant solution was extracted with methylene chloride. An organic layer was extracted with an aqueous 2N hydrochloric acid solution. After the extracted solution was made alkaline by an aqueous 2N sodium hydroxide, it was extracted with methylene chloride. An organic layer was dried, and the solvent was distilled to obtain 2.4 g of a crude product of 6-amino-4-cyano-2,2-bis(fluoromethyl)-2H-1-benzopyran.

NMR (CDCl$_3$)δ: 4.57(4H,d), 6.36(1H,s), 6.28–6.94(3H,m).
MS m/z: 236 (M$^+$)

(2) 10 ml of concentrated sulfuric acid was heated at 40° C. and 760 mg of sodium nitrite acid was added therein. Then, the reaction solution was cooled to room temperature and 20 ml of an acetic acid solution of 2.0 g of 6-amino-4-cyano-2,2-bis(fluoromethyl)-2H-1-benzopyran was added therein. The reaction solution was dropped into 12 ml of an aqueous hydrobromic acid solution of cuprous bromide prepared in advance from 4.2 g of copper (II) sulfate pentahydrate, 2.6 g of sodium bromide and 1.1 g of sodium sulfite under ice-cooling. The resultant mixture was heated to room temperature and stirred for 1 hour. Water was added therein and the mixture was extracted with methylene chloride. An organic layer was washed with an aqueous 2N hydrochloric acid solution and an aqueous 1N sodium hydroxide solution and dried. The solvent was distilled. The obtained residue was purified according to silica gel column chromatography (developing solution, AcOH:hexane=1:5) and recrystallized by a mixed solvent of ethyl acetate and hexane to obtain 690 mg of 6-bromo-4-cyano-2,2-bis(fluoromethyl)-2H-1-benzopyran with a melting point of 105°–107° C.

NMR (CDCl$_3$)δ: 4.55(4H,d), 6.41(1H,s), 6.75(1H,d), 7.13–7.83(2H,m).
MS m/z: 299 (M$^+$)

(3) Using 6-bromo-4-cyano-2,2-bis(fluoromethyl)-2H-1-benzopyran, 6-bromo-2,2-bis(fluoromethyl)-2H-1-benzopyran-4-carboxylic acid with a melting point of 165°–166° C. was obtained according to the same method as in Example 7 (2).

NMR (CDCl$_3$)δ: 4.58(4H,d), 6.55(1H,d), 7.29(1H,dd), 8.14 (1H,d), 9.82(1H,brs).
MS m/z: 318 (M$^+$)

(4) Using 6-bromo-2,2-bis(fluoromethyl)-2H-1-benzopyran-4-carboxylic acid, 6-bromo-N-(2-cyanoethyl)-2,2-bis(fluoromethyl)-2H-1-benzopyran-4-carboxamide with a melting point of 140°–142° C. was obtained according to the same method as in Example 10.

NMR (CDCl$_3$-CD$_3$OD)δ: 2.75(2H,t), 3.63(2H,t), 4.61(4H, d), 6.04(1H,s), 6.81(1H,d), 7.36(1H,dd), 7.69(1H,d).
MS m/z: 370 (M$^+$)

Example 22

6-Bromo-2,2-bis(fluoromethyl)-N-methyl-2H-1-benzopyran-4-carboxamide

Using 6-bromo-2,2-bis(fluoromethyl)-2H-1-benzopyran-4-carboxylic acid, 6-bromo-2,2-bis(fluoromethyl)-N-methyl-2H-1-benzopyran-4-carboxamide with a melting point of 187°–188° C. was obtained according to the same method as in Example 7 (3).

NMR (CDCl$_3$—CD$_3$OD)δ: 3.68(3H,s), 4.56(4H,d), 5.94 (1H,s), 6.77(1H,d), 7.31(1H,dd), 7.63(1H,d).
MS m/z: 331 (M$^+$)

Example 23

2,2-Bis(fluoromethyl)-6-trifluoromethyl-N-methyl-2H-1-benzopyran-4-carboxamide (1) A mixture of 41.7 g of 2,2-bis(fluoromethyl)-6-nitro-2H-1-benzopyran-4-carboxylic acid, 20 ml of sulfuric acid and 300 ml of ethyl alcohol was refluxed with heating for 6 hours. The reaction mixture was poured into ice water and crystals separated out were filtered to obtain 42.7 g of 2,2-bis(fluoromethyl)-6-nitro-2H-1-benzopyran-4-carboxylic acid ethyl ester with a melting point of 96°–98° C.

NMR (CDCl$_3$)δ: 1.42(3H,t), 4.38(2H,q), 4.58(4H,d), 6.69 (1H,s), 6.94(1H,d). 8.07(1H,dd), 8.92(1H,d).

MS m/z: 313 (M$^+$)

(2) Using 2,2-bis(fluoromethyl)-6-nitro-2H-1-benzopyran-4-carboxylic acid ethyl ester, an oily product of 6-amino-2,2-bis(fluoromethyl)-2H-1-benzopyran-4-carboxylic acid ethyl ester was obtained according to the same method as in Example 21 (1).

NMR (CDCl$_3$)δ: 1.31(3H,t), 3.0–4.0(2H,m), 4.36(2H,q), 4.55(4H,d), 6.2–6.9(3H,m), 7.26(1H,d).

MS m/z: 283 (M$^+$)

(3) To a mixture of 4.0 g of 6-amino-2,2-bis (fluoromethyl)-2H-1-benzopyran-4-carboxylic acid ethyl ester, 1.66 g of sulfuric acid and 40 ml of water was added a mixture of 1.09 g of sodium nitrite, 10 ml of methylene chloride and 10 ml of water under ice-cooling. The mixture was stirred under ice-cooling for 10 minutes. Further, to the reaction mixture was added a mixture of 2.85 g of potassium iodide and 5 ml of water, and the mixture was stirred at room temperature for 1.5 hours. To the reaction mixture solution was added water and the resultant solution was extracted with methylene chloride. An organic layer was washed with a 20% aqueous sodium sulfite solution and a saturated saline solution, dried over sodium sulfate and concentrated under reduced pressure. The obtained residue was subjected to silica gel column chromatography (developing solution, ethyl acetate:hexane=10:1) to obtain 3.67 g of 2,2-bis (fluoromethyl)-6-iodo-2H-1-benzopyran-4-carboxylic acid ethyl ester with a melting point of 89°–90° C.

NMR (CDCl$_3$)δ: 1.39(3H,t), 4.33(2H,q), 4.58(4H,d), 6.60 (1H,s), 6.67(1H,d), 7.02(1H,dd), 8.30(1H,d).

MS m/z: 394 (M$^+$)

(4) A mixture of 1.00 g of 2,2-bis(fluoromethyl)-6-iodo-2H-1-benzopyran-4-carboxylic acid ethyl ester, 0.84 g of potassium trifluoroacetate, 1.18 g of cuprous iodide, 4 ml of toluene and 10 ml of N,N-dimethylformamide was stirred with heating under an atmosphere of a nitrogen gas with removing toluene at 150° C. for 5.5 hours. To the reaction mixture was added a mixed solution of 2N hydrochloric acid and ethyl acetate and insolubles were filtered using Celite. An organic layer was separated from the filtrate and a water layer was extracted with ethyl acetate. It was washed together with the obtained organic layer with a saturated saline solution, dried over sodium sulfate and concentrated under reduced pressure. The obtained residue was subjected to silica gel column chromatography (developing solution, ethyl acetate:hexane =10:1) to obtain 0.51 g of an oily product of 2,2-bis(fluoromethyl)-6-trifluoromethyl-2H-1-benzopyran-4-carboxylic acid ethyl ester.

NMR (CDCl$_3$)δ: 1.36(3H,t), 4.31(2H,q), 4.53(4H,d), 6.63 (1H,s), 6.94(1H,d), 7.47(1H,dd), 8.31(1H,d).

MS m/z: 336 (M$^+$)

(5) A mixture of 0.51 g of 2,2-bis(fluoromethyl)-6-trifluoromethyl-2H-1-benzopyran-4-carboxylic acid ethyl ester, 0.13 g of potassium hydroxide and 10 ml of ethyl alcohol was stirred at room temperature for 2 hours. To the reaction mixture was added ice water and hydrochloric acid and crystals separated out were filtered to obtain 0.43 g of 2,2-bis(fluoromethyl)-6-trifluoromethyl-2H-1-benzopyran-4-carboxylic acid.

MS m/z: 308 (M$^+$)

(6) Using 2,2-bis(fluoromethyl)-6-trifluoromethyl-2H-1-benzopyran-4-carboxylic acid, 2,2-bis(fluoromethyl)-6-trifluoromethyl-N-methyl-2H-1-benzopyran-4-carboxamide with a melting point of 162°–164° C. was obtained according to the same method as in Example 7 (3).

NMR (CDCl$_3$)δ: 2.88(3H,d), 4.53(4H,d), 5.99(1H,s), 6.48 (1H,brs), 6.95(1H,d), 7.48(1H,dd), 7.82(1H,d).

MS m/z: 321 (M$^+$)

Example 24

2,2-Bis(fluoromethyl)-6-trifluoromethyl-N-methyl-2H-1-benzopyran-4-carbothioamide Using 2,2-bis(fluoromethyl)-6-trifluoromethyl-N-methyl-2H-1-benzopyran-4-carboxamide, 2,2-bis(fluoromethyl)-6-trifluoromethyl-N-methyl-2H-1-benzopyran-4-carbothioamide with a melting point of 145°–147° C. was obtained according to the same method as in Example 8.

NMR (CDCl$_3$)δ: 3.25(3H,d). 4.54(4H,d), 5.77(1H,s), 6.93 (1H,d). 7.44(1H,dd), 7.54(1H,brs), 7.66(1H,d).

MS m/z: 337 (M$^+$)

Example 25

N-(2-Cyanoethyl)-2,2-bis(fluoromethyl)-6-trifluoromethyl-2H-1-benzopyran-4-carboxamide Using 2,2-bis(fluoroemthyl)-6-trifluoromethyl-2H-1-benzopyran-4-carboxylic acid, N-(2-cyanoethyl)-2,2-bis (fluoromethyl)-6-trifluoromethyl-2H-1-benzopyran-4-carboxamide with a melting point of 135°–136° C. was obtained according to the same method as in Example 10.

NMR (CDCl$_3$)δ: 2.70(2H,t), 3.63(2H,q), 4.57(4H,d), 6.08 (1H,s), 6.96(1H,brs), 6.98(1H,d), 7.50(1H,dd), 7.84(1H, d).

MS m/z: 360 (M$^+$)

Example 26

6-Pentafluoroethyl-2,2-bis(fluoromethyl)-N-methyl-2H-1-benzopyran-4-carboxamide (1) Using 2,2-bis(fluoromethyl)-6-iodo-2H-1-benzopyran-4-carboxylic acid ethyl ester and potassium pentafluoropropionate, an oily product of 6-pentafluoroethyl-2,2-bis(fluoromethyl)-2H-1-benzopyran-4-carboxylic acid ethyl ester was obtained according to the same method as in Example 23 (4).

NMR (CDCl$_3$)δ: 1.40(3H,t), 4.38(2H,q), 4.60(4H,d), 6.69 (1H,s), 7.00(1H,d), 7.45(1H,dd), 8.30(1H,d).

MS m/z: 386 (M$^+$)

(2) Using 6-pentafluoroethyl-2,2-bis(fluoromethyl)-2H-1-benzopyran-4-carboxylic acid ethyl ester, 6-pentafluoroethyl-2,2-bis(fluoromethyl)-2H-1-benzopyran-4-carboxylic acid was obtained according to the same method as in Example 23 (5).

MS m/z: 358 (M$^+$)

(3) Using 6-pentafluoroethyl-2,2-bis(fluoromethyl)-2H-1-benzopyran-4-carboxylic acid, 6-pentafluoroethyl-2,2-bis (fluoromethyl)-N-methyl-2H-1-benzopyran-4-carboxamide with a melting point of 127°–128° C. was obtained according to the same method as in Example 7 (3).

NMR (CDCl$_3$)δ: 2.82(3H,d), 4.46(4H,d), 5.93(1H,s), 6.82 (1H,brs), 6.92(1H,d), 7.40(1H,dd), 7.72(1H,d).

MS m/z: 371 (M$^+$)

Example 27

6-Pentafluoroethyl-2,2-bis(fluoromethyl)-N-methyl-2H-1-benzopyran-4-carbothioamide Using 6-pentafluoroethyl-2,2-bis(fluoromethyl)-N-methyl-2H-1-benzopyran-4-carboxamide, 6-pentafluoroethyl-2,2-bis(fluoromethyl)-N-methyl-2H-1-benzopyran-4-carbothioamide with a melting point of 148°–149° C. was obtained according to the same method as in Example 8.

NMR (CDCl$_3$)δ: 3.27(3H,d), 4.53(2H,d), 4.56(2H,d), 5.80 (1H,s), 6.97(1H,d), 7.40(1H,dd), 7.55(1H,brs), 7.63(1H, d).

MS m/z: 387 (M$^+$)

Example 28

N-Cyano-6-pentafluoroethyl-2,2-bis(fluoromethyl)-N'-methyl-2H-1-benzopyran-4-amidine A mixture of 0.14 g of 6-pentafluoroethyl-2,2-bis(fluoromethyl)-N-methyl-2H-1-benzopyran-4-carbothioamide, 0.31 g of ethyl iodide, 0.017 g of sodium hydride and 5 ml of tetrahydrofuran was refluxed with heating for 45 minutes. To the reaction mixture were added 0.081 g of cyanamide and 0.017 g of sodium hydride and the resultant mixture was refluxed with heating for 22 hours. To the reaction mixture was added a small amount of hydrochloric acid and the mixture was concentrated under reduced pressure. The resultant residue was subjected to silica gel column chromatography (developing solution, ethyl acetate:hexane=1:1) to obtain 0.07 g of N-cyano-6-pentafluoroethyl-2,2-bis(fluoromethyl)-N'-methyl-2H-1-benzopyran-4-amidine with a melting point of 178°–179° C.

NMR (CDCl$_3$)δ: 2.88(3H,d), 4.56(4H,d), 5.88(1H,s), 6.98 (1H,d), 7.12(1H,d), 7.46(1H,dd), 7.72(1H,brs).

MS m/z: 395 (M$^+$)

Example 29

N-(2-Cyanoethyl)-6-pentafluoroethyl-2,2-bis(fluoromethyl)-2H-1-benzopyran-4-carboxamide Using 6-pentafluoroethyl-2,2-bis(fluoromethyl)-2H-1-benzopyran-4-carboxylic acid, N-(2-cyanoethyl)-6-pentafluoroethyl-2,2-bis(fluoromethyl)-2H-1-benzopyran-4-carboxamide with a melting point of 144°–145° C. was obtained according to the same method as in Example 10.

NMR (CDCl$_3$)δ: 2.72(2H,t), 3.65(2H,q), 4.60(4H,d), 6.09 (1H,s), 6.80(1H,brs), 7.02(1H,d), 7.52(1H,dd), 7.83(1H, d)

MS m/z: 410 (M$^+$)

Example 30

2,2-Bis(fluoromethyl)-6-heptafluoropropyl-N-methyl-2H-1-benzopyran-4-carboxamide (1) Using 2,2-bis(fluoromethyl)-6-iodo-2H-1-benzopyran-4-carboxylic acid ethyl ester and potassium heptafluorobutyrate, an oily product of 2,2-bis(fluoromethyl)-6-heptafluoropropyl-2H-1-benzopyran-4-carboxylic acid ethyl ester and an oily product of 2,2-bis(fluoromethyl)-2H-1-benzopyran-4-carboxylic acid ethyl ester were obtained according to the same method as in Example 23 (4). 2,2-Bis(fluoromethyl)-6-heptafluoropropyl-2H-1-benzopyran-4-carboxylic acid ethyl ester:

NMR (CDCl$_3$)δ: 1.36(3H,t), 4.32(2H,q), 4.57(4H,d), 6.69 (1H,s), 7.02(1H,d), 7.46(1H,dd), 8.29(1H,d).

MS m/z: 436 (M$^+$)

2,2-Bis(fluoromethyl)-2H-1-benzopyran-4-carboxylic acid ethyl ester:

NMR (CDCl$_3$)δ: 1.38(3H,t), 4.34(2H,q), 4.58(4H,d), 6.58 (1H,s), 6.8–7.5(3H,m), 7.94(1H,dd).

MS m/z: 268 (M$^+$)

(2) Using 2,2-bis(fluoromethyl)-6-heptafluoropropyl-2H-1-benzopyran-4-carboxylic acid ethyl ester, 2,2-bis(fluoromethyl)-6-heptafluoropropyl-2H-1-benzopyran-4-carboxylic acid was obtained according to the same method as in Example 23 (5).

MS m/z: 408 (M$^+$)

(3) Using 2,2-bis(fluoromethyl)-6-heptafluoropropyl-2H-1-benzopyran-4-carboxylic acid, an oily product of 2,2-bis(fluoromethyl)-6-heptafluoropropyl-N-methyl-2H-1-benzopyran-4-carboxamide as in Example 7 (3).

NMR (CDCl$_3$)δ: 2.94(3H,d), 4.59(4H,d), 6.02(1H,s), 6.39 (1H,brs), 7.01(1H,d), 7.47(1H,dd), 7.82(1H,d).

MS m/z: 421 (M$^+$)

Example 31

2,2-Bis(fluoromethyl)-6-heptafluoropropyl-N-methyl-2H-1-benzopyran-4-carbothioamide Using 2,2-bis(fluoromethyl)-6-heptafluoropropyl-N-methyl-2H-1-benzopyran-4-carboxamide, 2,2-bis(fluoromethyl)-6-heptafluoropropyl-N-methyl-2H-1-benzopyran-4-carbothioamide with a melting point of 125°–126° C. was obtained according to the same method as in Example 8.

NMR (CDCl$_3$)δ: 3.24(3H,d), 4.55(4H,d), 5.82(1H,s), 6.98 (1H,d), 7.42(1H,dd), 7.55(1H,brs), 7.62(1H,d).

MS m/z: 437 (M$^+$)

Example 32

N-(2-Cyanoethyl)-2,2-bis(fluoromethyl)-6-heptafluoropropyl-2H-1-benzopyran-4-carboxamide Using 2,2-bis(fluoromethyl)-6-heptafluoropropyl-2H-1-benzopyran-4-carboxylic acid, N-(2-cyanoethyl)-2,2-bis(fluoromethyl)-6-heptafluoropropyl-2H-1-benzopyran-4-carboxamide with a melting point of 135°–136° C. was obtained according to the same method as in Example 10.

NMR (CDCl$_3$)δ: 2.70(2H,t), 3.62(2H,q), 4.58(4H,d), 6.05 (1H,s), 6.80(1H,brs), 6.98(1H,d), 7.43(1H,dd), 7.78(1H, d).

MS m/z: 460 (M$^+$)

Example 33

2,2-Bis(fluoromethyl)-N-methyl-2H-1-benzopyran-4-carboxamide (1) Using 2,2-bis(fluoromethyl)-2H-1-benzopyran-4-carboxylic acid ethyl ester, 2,2-bis(fluoromethyl)-2H-1-benzopyran-4-carboxylic acid was obtained according to the same method as in Example 23 (5).

MS m/z: 240 (M$^+$)

(2) Using 2,2-bis(fluoromethyl)-2H-1-benzopyran-4-carboxylic acid, 2,2-bis(fluoromethyl)-N-methyl-2H-1-benzopyran-4-carboxamide with a melting point of 138°–139° C. was obtained according to the same method as in Example 7 (3).

NMR (CDCl$_3$)δ: 2.85(3H,d), 4.49(4H,d), 5.86(1H,s), 6.11 (1H,brs), 6.7–7.5(4H,m).

MS m/z: 253 (M$^+$)

Example 34

N-(2-cyanoethyl)-2,2-bis(fluoromethyl)-2H-1-benzopyran-4-carboxamide

Using 2,2-bis(fluoromethyl)-2H-1-benzopyran-4-carboxylic acid, an oily product of N-(2-cyanoethyl)-2,2-bis (fluoromethyl)-2H-1-benzopyran-4-carboxamide was obtained according to the same method as in Example 10.
NMR (CDCl$_3$)δ: 2.71(2H,t), 3.62(2H,q), 4.57(4H,d), 5.99 (1H,s), 6.2–7.6(5H,m).
MS m/z: 292 (M$^+$)

Example 35

6-Cyano-2,2-bis(fluoromethyl)-N-methyl-2H-1-benzopyran-4-carboxamide (1) A mixture of 0.40 g of 2,2-bis(fluoromethyl)-6-iodo-2H-1-benzopyran-4-carboxylic acid ethyl ester, 0.11 g of Cuprous cyanide and 3 ml of N,N-dimethylformamide was stirred with heating at 150° C. for 2 hours. To the reaction mixture was added 2N hydrochloric acid solution. The resultant mixture was extracted with ethyl acetate, washed with a saturated saline solution and dried over sodium sulfate. It was concentrated under reduced pressure. The obtained residue was subjected to silica gel column chromatography (developing solution, ethyl acetate:hexane=3:1) to obtain 0.22 g of 6-cyano-2,2-bis(fluoromethyl-2H-1-benzoyran-4-carboxylic acid ethyl ester with a melting point of 115°–117° C.
NMR (CDCl$_3$)δ: 1.34(3H,t), 4.31(2H,q), 4.54(4H,d), 6.68 (1H,s), 6.90(1H,d), 7.45(1H,dd), 8.33(1H,d).
MS m/z: 293 (M$^+$)

(2) Using 6-cyano-2,2-bis(fluoromethyl)-2H-1-benzopyran-4-carboxylic acid ethyl ester, 6-cyano-2,2-bis(fluoromethyl)-2H-1-benzopyran-4-carboxylic acid with a melting point of 165°–167° C. was obtained according to the same method as in Example 23 (5).
MS m/z: 265 (M$^+$)

(3) Using 6-cyano-2,2-bis(fluoromethyl)-2H-1-benzopyran-4-carboxylic acid, 6-cyano-2,2-bis(fluoromethyl)-N-methyl-2H-1-benzopyran-4-carboxamide with a melting point of 206°–207° C. was obtained according to the same method as in Example 7 (3).
NMR (DMSO-d$_6$)δ: 2.73(3H,d), 4.66(4H,d), 6.13(1H,s), 7.07(1H,d), 7.68(1H,dd), 7.86(1H,d), 8.4–8.6(1H,m).
MS m/z: 278 (M$^+$)

Example 36

6-Cyano-N-(2-cyanoethyl)-2,2-bis(fluoromethyl)-2H-1-benzopyran-4-carboxamide

Using 6-cyano-2,2-bis(fluoromethyl)-2H-1-benzopyran-4-carboxylic acid, 6-cyano-N-(2-cyanoethyl)-2,2-bis(fluoromethyl)-2H-1-benzopyran-4-carboxamide with a melting point of 170°–172° C. was obtained according to the same method as in Example 10.
NMR (DMSO-d$_6$)δ: 2.78(2H,t), 3.47(2H,q), 4.66(4H,d), 6.14(1H,s), 7.09(1H,d), 7.72(1H,dd), 7.87(1H,d), 8.8–9.0 (1H,m).
MS m/z: 317 (M$^+$)

Example 37

N-(2-Cyanoethyl-2,2-bis(fluoromethyl)-3,4-dihydro-6-nitro-2H-1-benzopyran-4-carboxamide A mixture of 0.33 g of N-(2-cyanoethyl)-2,2-bis(fluoromethyl)-6-nitro-2H-1-benzopyran-4-carboxamide, 0.20 g of sodium borohydride, 20 ml of tetrahydrofuran and 10 ml of methyl alcohol was stirred at room temperature for 30 minutes. The reaction mixture was concentrated under reduced pressure and 2N hydrochloric acid was added therein. The resultant mixture was extracted with ethyl acetate, dried over magnesium sulfate and concentrated under reduced pressure. The obtained residue was subjected to silica gel column chromatography (developing solution, ethyl acetate:hexane=1.1) to obtain 0.17 g of N-(2-cyanoethyl)-2,2-bis(fluoromethyl)-3,4-dihydro-6-nitro-2H-1-benzopyran-4-carboxamide with a melting point of 137°–138° C.
NMR (CDCl$_3$-DMSO-d$_6$)δ: 2.35(2H,dd), 2.67(2H,t), 3.54 (2H,q), 3.6–4.2(1H,m), 4.55(4H,d), 6.97(1H,d), 7.9–8.2 (2H,m), 8.64(1H,brs).
MS m/z: 339 (M$^+$)

Example 38

N-(2-Cyanoethyl)-2,2-bis(fluoromethyl)-3,4-dihydro-6-nitro-2H-1-benzopyran-4-carbothioamide Using N-(2-cyanoethyl)-2,2-bis(fluoromethyl)-6-nitro-2H-1-benzopyran-4-carbothioamide, N-(2-cyanoethyl)-2,2-bis(fluoromethyl)-3,4-dihydro-6-nitro-2H-1-benzopyran-4-carbothioamide with a melting point of 183°–184° C. was obtained according to the same method as in Example 37.
NMR (CDCl$_3$-DMSO-d$_6$)δ: 2.2–3.3(4H,m), 2.8–4.7(3H,m), 4.62(4H,d), 7.04(1H,d), 8.03(1H,d), 8.10(1H,dd), 10.73 (1H,brs).
MS m/z: 355 (M$^+$)

Example 39

6-Amino-N-(2-cyanoethyl)-2,2-bis(fluoromethyl)-2H-1-benzopyran-4-carboxamide hydrochloride (1) Using N-(2-cyanoethyl)-2,2-bis(fluoromethyl)-6-nitro-2H-1-benzopyran-4-carboxamide, 0.34 g of 6-amino-N-(2-cyano-ethyl)-2,2-bis(fluoromethyl)-2H-1-benzopyran-4-carboxamide was obtained as an oil according to the same method as in Example 21 (1).
NMR (CDCl$_3$)δ: 2.59(2H,t), 3.1–3.9(4H,m), 4.48(4H,d), 5.90(1H,s), 6.4–7.0(3H,m), 7.30(1H,brs).
MS m/z: 307 (M$^+$)

(2) To 0.34 g of 6-amino-N-(2-cyanoethyl)-2,2-bis-(fluoromethyl)-2H-1-benzopyran-4-carboxamide were added methyl alcohol and a small amount of concentrated hydrochloric acid. The mixture was condensed under reduced pressure to obtain 0.35 g of 6-amino-N-(2-cyanoethyl)-2,2-bis(fluoromethyl)-2H-1-benzopyran-4-carboxamide hydrochloride with a melting point of 202°–205° C.
NMR (DMSO-d$_6$)δ: 2.77(2H,t), 3.45(2H,q), 4.64(4H,d), 6.11(1H,s), 7.00(1H,d), 7.18(1H,dd), 7.51(1H,d), 9.3–10.2(1H,m).

Example 40

N-(2-Cyanoethyl)-2,2-bis(fluoromethyl)-6-iodo-2H-1-benzopyran-4-carboxamide

Using 6-amino-N-(2-cyanoethyl)-2,2-bis(fluoromethyl)-H-1-benzopyran-4-carboxamide hydrochloride, N-(2-cyanoethyl)-2,2-bis(fluoromthyl)-6-iodo-2H-1-benzoyran-4-carboxamide with a melting point of 130°–132° C. was obtained according to the same method as in Example 23 (3).
NMR (CDCl$_3$)δ: 2.87(2H,t), 3.75(2H,q), 4.68(4H,d), 6.09 (1H,s), 6.76(1H,d), 6.87(1H,brs), 7.64(1H,dd), 7.92(1H, d).
MS m/z: 394 (M$^+$)

Example 41

N-(2-Cyanoethyl)-6-pentafluoroethyl-2,2-bis(fluoromethyl)-2H-1-benzopyran-4-carboxamide Using N-(2-cyanoethyl)-2,2-bis(fluoromethyl)-6-iodo-2H-1-benzopyran-4-carboxamide, N-(2-cyanoethyl)-6- pentafluoroethyl- 2,2-bis(fluoromethyl)-2H-1-benzopyran-4-carboxamide represented in Example 29 was obtained according to the same method as in Example 26 (1).

Example 42

2-Fluoromethyl-N,2-dimethyl-6-nitro-2H-1-benzopyran-4-carboxamide (1) To 8.24 g of 2-fluoromethyl-2-methyl-6-nitro-2H-1-benzopyran dissolved in 100 ml of chloroform was added dropwise 2.7 ml of bromine with stirring under cooling with water, and the mixture was stirred for 20 hours at room temperature. After the solvent was removed, 100 ml of dioxane and 2N NaOH solution were added to the residue and stirred at room temperature for 16 hours. When ice-water was added to the reaction mixture, crystals were separated out. The crystals were collected by filtration, washed with water and dissolved in methylene chloride. It was washed with water and dried. The solvent was evaporated off to obtain 11.01 g of 4-bromo-2-fluoromethyl-2-methyl-6-nitro-2H-1-benzopyran with a melting point of 116°–117° C.

NMR (CDCl$_3$)$\delta$: 1.48(3H,d), 4.32(2H,d), 6.06(1H,s), 6.81 (1H,d), 8.00(1H,dd), 8.25(1H,d).

MS m/z: 301 (M$^+$)

(2) A mixture of 5.6 g of 4-bromo-2-fluoromethyl-2-methyl-6-nitro-2H-1-benzopyran, 1.84 g of cuprous cyanide and 50 ml of N,N-dimethylformamide was refluxed with heating for 5 hours under a nitrogen atmosphere. When aqueous HCl solution was added to the mixture under ice-cooling, crystals were separated out. The crystals were collected by filtration, washed with water and dissolved in methylene chloride. After it washed with water and dried, the solvent was evaporated off. The resultant residue was purified with silica gel column chromatography (developing solution: CH$_2$Cl$_2$) to obtain 3.27 g of 4-cyano-2-fluoromethyl-2-methyl-6-nitro-2H-1-benzopyran with a melting point of 169°–171° C.

NMR (CDCl$_3$)$\delta$: 1.54(3H,d), 4.44(2H,d), 6.47(1H,s), 6.93 (1H,dd), 8.08(1H,dd), 8.17(1H,brs).

MS m/z: 248 (M$^+$)

(3) Using 4-cyano-2-fluoromethyl-2-methyl-6-nitro-2H-1-benzopyran, 2-fluoromethyl-2-methyl-6-nitro-2H-1-benzoyran-4-carboxylic acid with a melting point of 195°–198°° C. was obtained according to the same method as in Example 7 (2).

NMR (CDCl$_3$-DMSO-d$_6$)$\delta$: 1.48(3H,d), 4.45(2H,d), 6.76 (1H,s), 6.88(1H,d), 8.00(1H,dd), 8.72(1H,brs), 8.98(1H, d).

MS m/z: 267 (M$^+$)

(4) Using 2-fluoromethyl-2-methyl-6-nitro-2H-1-benzopyran-4-carboxylic acid, 2-fluoromethyl-N,2-dimethyl-6-nitro-2H-1-benzopyran-4-carboxamide with a melting point of 171°–173° C. was obtained according to the same method as in Example 7 (3).

NMR (CDCl$_3$-DMSO-d$_6$)$\delta$: 1.46(3H,d), 2.82(3H,d), 4.37 (2H,d), 6.00(1H,s), 6.80(1H,d), 7.65–8.14(1H,m), 7.92 (1H,dd), 8.40(1H,d).

MS m/z: 280 (M$^+$)

Example 43

2-Fluoromethyl-N,2-dimethyl-6-nitro-2H-1-benzopyran-4-carbothioamide

Using 2-fluoromethyl-N,2-dimethyl-6-nitro-2H-1-benzopyran-4-carboxamide, 2-fluoromethyl-N,2-dimethyl-6-nitro-2H-1-benzopyran-4-carbothioamide with a melting point of 141°–144° C. was obtained according to the same method as in Example 8.

NMR (CDCl$_3$)$\delta$: 1.43(3H,d). 3.15(3H,d), 4.30(2H,d), 5.67 (1H,s), 6.72(1H,d), 7.82(1H,dd), 8.14(1H,d), 8.24(1H, brs).

MS m/z: 296 (M$^+$)

Example 44

N-(2-Cyanoethyl)-2-fluoromethyl-2-methyl-6-nitro-2H-1-benzopyran-4-carboxamide

Using 2-fluoromethyl-2-methyl-6-nitro-2H-1-benzopyran-4-carboxylic acid, N-(2-cyanoethyl)-2-fluoromethyl-2-methyl-6-nitro-2H-1-benzoyran-4-carboxamide with a melting point of 165°–167° C. was obtained according to the same method as in Example 19.

NMR (CDCl$_3$-DMSO-d$_6$)$\delta$: 1.48(3H,d), 2.72(2H,t), 3.58 (2H,dt), 4.41(2H,d), 6.14(1H,s), 6.87(1H,d), 7.99(1H,dd), 8.48(1H,d), 8.58(1H,brs).

MS m/z: 319 (M$^+$)

Example 45

N-(2-Cyanoethyl)-2-fluoromethyl-2-methyl-6-nitro-2H-1-benzopyran-4-carbothioamide Using N-(2-cyanoethyl)-2-fluoromethyl-2-methyl-6-nitro-2H-1-benzopyran-4-carboxamide, N-(2-cyanoethyl)-2-fluoromethyl-2-methyl-6-nitro-2H-1-benzopyran-4-carbothioamide was obtained as oil according to the same method as in Example 16.

NMR (CDCl$_3$)$\delta$: 1.47(3H,d), 2.88(2H,t), 3.98(2H,dt), 4.36 (2H,d), 5.80(1H,s), 6.81(1H,d), 7.92(1H,dd), 8.23(1H,d), 8.51(1H,brt).

MS m/z: 335 (M$^+$)

Example 46

2-Trifluoromethyl-N,2-dimethyl-6-nitro-2H-1-benzopyran-4-carboxamide (1) Using 2-trifluoromethyl-2-methyl-6-nitro-2H-1-benzopyran, 4-bromo-2-trifluoromethyl-2-methyl-6-nitro-2H-1-benzopyran was obtained as oil according to the same method as in Example 42 (1).

NMR (CDCl$_3$)$\delta$: 1.68(3H,s), 6.13(1H,s), 6.93(1H,d), 8.28 (1H,dd), 8.34(1H,d).

MS m/z: 337 (M$^+$)

(2) Using 4-bromo-2-trifluoromethyl-2-methyl-6-nitro-2H-1-benzopyran, 4-cyano-2-trifluoromethyl-2-methyl-6-nitro-2H-1-benzopyran with a melting point of 105°–107° C. was obtained according to the same method as in Example 42 (2).

NMR (CDCl$_3$)$\delta$: 1.77(3H,s), 6.48(1H,s), 7.05(1H,d), 8.24 (1H,dd), 8.31(1H,d).

MS m/z: 284 (M$^+$)

(3) Using 4-cyano-2-trifluoromethyl-2-methyl-6-nitro-2H-1-benzopyran, 2-trifluoromethyl-2-methyl-6-nitro-2H-1-benzopyran-4-carboxylic acid with a melting point of 172°–174° C. was obtained according to the same method as in Example 7 (2).

NMR (CDCl$_3$)$\delta$: 1.73(3H,s), 6.81(1H,s), 6.90(1H,d), 8.04 (1H,dd), 8.93(1H,d), 9.49(1H,brs).

MS m/z: 303 (M$^+$)

(4) Using 2-trifluoromethyl-2-methyl-6-nitro-2H-1-benzopyran-4-carboxylic acid, 2-trifluoromethyl-N,2-dimethyl-6-nitro-2H-1-benzopyran-4-carboxamide with a melting point of 196°–197° C. was obtained according to the same method as In Example 7 (3).

NMR (CDCl$_3$)δ: 1.68(3H,s), 2.99(3H,d), 5.99(1H,s), 5.78–6.47(1H,m), 6.97(1H,d), 8.11(1H,dd), 8.45(1H,d).
MS m/z: 316 (M$^+$)

Example 47

2-Trifluoromethyl-N,2-dimethyl-6-nitro-2H-1-benzopyran-4-carbothioamide

Using 2-trifluoromethyl-N,2-dimethyl-6-nitro-2H-1-benzopyran-4-carboxamide, 2-trifluoromethyl-N,2-dimethyl-6-nitro-2H-1-benzopyran-4-carbothioamide with a melting point of 158°–160° C. was obtained according to the same method as in Example 8.
NMR (CDCl$_3$)δ: 1.68(3H,s), 3.27(3H,d), 5.82(1H,d), 6.92 (1H,d), 8.00(1H,dd), 8.28(1H,d), 8.03–8.48(1H,m).
MS m/z: 332 (M$^+$)

Example 48

N-(2-Cyanoethyl)-2-trifluoromethyl-2-methyl-6-nitro-2H-1-benzopyran-4-carboxamide Using 2-trifluoromehtyl-2-methyl-6-nitro-2H-1-benzopyran-4-carboxylic acid, N-(2-cyanoethyl)-2-trifluoromethyl-2-methyl-6-nitro-2H-1-benzopyran-4-carboxamide with a melting point of 191°–193° C. was obtained according to the same method as in Example 10.
NMR (DMSO-d$_6$)δ: 1.72(3H,s), 2.80(2H,t), 8.50(2H,q), 6.32(1H,s), 7.20(1H,d), 8.18(1H,dd), 8.49(1H,d), 9.07 (1H,brt).
MS m/z: 355 (M$^+$)

Example 49

N-(2-Cyanoethyl)-2-trifluoromethyl-2-methyl-6-nitro-2H-1-benzopyran-4-carbothioamide Using N-(2-cyanoethyl)-2-trifluoromethyl-2-methyl-6-nitro-2H-1-benzopyran-4-carboxamide, N-(2-cyanoethyl)-2-trifluoromethyl-2-methyl-6-nitro-2H-1-benzopyran-4-carbothioamide was obtained as an oil according to the same method as in Example 16.
NMR (CDCl$_3$)δ: 1.69(3H,s), 2.93(2H,t), 4.07(2H,q), 5.83 (1H,s), 6.83(1H,d), 8.05(1H,dd), 8.38(1H,d), 8.76(1H, brt).
MS m/z: 371 (M$^+$)

Example 50

6-Nonafluorobutyl-2,2-bis(fluoromethyl)-N-methyl-2H-1-benzopyran-4-carboxamide (1) A mixture of 0.30 g of ethyl 2,2-bis(fluoromethyl)-6-iodo-2H-1-benzopyran-4-carboxylate, 3.50 g of nonafluorobutyl iodide, 0.30 g of copper powder, 0.32 g of cuprous iodide and 3 ml of hexamethylphosphoric triamide was stirred with heating at 70° C. for 22 hours, added another 1.75 g of nonafluorobutyl iodide, and stirred with heating at 150° C. for 5 hours. A mixture of 2N HCl and ethyl acetate was added to the reaction mixture, and insoluble materials were separated off using a celite. An organic layer was taken up, and an aqueous layer was extracted with ethyl acetate. The organic layers were combined, washed with saturated sodium chloride solution, dried over sodium sulfate, and concentrated in vacuo. The resultant residue was purified with silica gel column chromatography (developing solution, methylene chloride:hexane=5:1) to obtain 0.19 g of ethyl 6-nonafluorobutyl-2,2-bis(fluoromethyl)-2H-1-benzopyran-4-carboxylate as an oil.
NMR (CDCl$_3$)δ: 1.38(3H,t), 4.36(2H,q), 4.59(4H,d), 6.68 (1H,s), 7.01(1H,d), 7.48(1H,dd), 8.30(1H,d).
MS m/z: 486 (M$^+$)

(2) A mixture of 0.19 g of ethyl 6-nonafluorobutyl-2,2-bis(fluoromethyl)-2H-1-benzopyran-4-carboxylate, 0.03 g of KOH and 3 ml of ethyl alcohol was stirred at room temperature for 1 hour. Ice water and HCl were added to the reaction mixture, and the precipitated crystals were collected by filtration to obtain 0.15 g of 6-nonafluoro-butyl-2,2-bis (fluoromethyl)-2H-1-benzopyran-4-carboxylic acid with a melting point of 180°–181° C.
MS m/z: 458 (M$^+$)

(3) Using 6-nonafluorobutyl-2,2-bis(fluoromethyl)-2H-1-benzopyran-4-carboxylic acid, 6-nonafluorobutyl-2,2-bis (fluoromethyl)-N-methyl-2H-1-benzopyran-4-carboxamide was obtained as an oil according to the same method as in Example 7 (3).
NMR (CDCl$_3$)δ: 2.94(3H,d), 4.56(4H,d), 5.92(1H,brs), 5.98 (1H,s), 6.99(1H,d), 7.45(1H,dd), 7.78(1H,d).
MS m/z: 471 (M$^+$)

Example 51

N-(2-Cyanoethyl)-6-nonafluorobutyl-2,2-bis(fluoromethyl)-2H-1-benzopyran-4-carboxamide Using 6-nonafluorobutyl-2,2-bis(fluoromethyl)-2H-1-benzopyran-4-carboxylic acid, N-(2-cyanoethyl)-6-nonafluorobutyl-2,2-bis(fluoromethyl)-2H-1-benzopyran-4-carboxamide with a melting point of 85°–86° C. was obtained according to the same method as in Example 10.
NMR (CDCl$_3$)δ: 2.69(2H,t), 3.60(2H,q), 4.55(4H,d), 6.08 (1H,s), 6.83(1H,brs), 6.99(1H,d), 7.47(1H,dd), 7.81(1H, d).
MS m/z: 510 (M$^+$)

Example 52

6-Chloro-2,2-bis(fluoromethyl)-N-methyl-2H-1-benzopyran-4-carboxamide (1) A mixture of 0.41 g of ethyl 6-amino-2,2-bis (fluoromethyl)-2H-1-benzopyran-4-carboxylate hydrochloride, 0.13 g of sulfuric acid, 0.10 g of sodium nitrite and 12 ml of H$_2$O was stirred under ice-cooling for 1 hour. The reaction mixture was added dropwise to a mixture of 0.30 g of cuprous chloride and 10 ml of concentrated HCl under ice-cooling, then the mixture was stirred at room temperature for 3 hours followed by 3 hours at 70° C. with heating. Added 2N HCl to the reaction mixture and extracted with ethyl acetate. The resultant organic layer was washed with saturated sodium chloride solution, dried over sodium sulfate and concentrated in vacuo. To the residue thus obtained added a mixture of 50 ml of ethyl alcohol and 2 ml of sulfuric acid and refluxed with heating for 2 hours. The reaction mixture was concentrated in vacuo to half a volume, added water to the residue and extracted with methylene chloride. The resultant organic layer was washed with saturated sodium chloride solution, dried over sodium sulfate and concentrated in vacuo. The residue thus obtained was purified with silica gel column chromatography (developing solution, ethyl acetate:hexane=1:10) to obtain 0.07 g of ethyl 6-chloro-2,2-bis(fluoromethyl)-2H-1-benzopyran-4-carboxylate with a melting point of 76°–78° C.
NMR (CDCl$_3$)δ: 1.37(3H,t), 4.31(2H,q), 4.54(4H,d), 6.62 (1H,s), 6.81(1H,d), 7.18(1H,dd), 7.98(1H,d).
MS m/z: 302 (M$^+$)

(2) A mixture of 0.07 g of ethyl 6-chloro-2,2-bis (fluoromethyl)-2H-1-benzopyran-4-carboxylate, 0.05 g of KOH and 3 ml of ethyl alcohol was stirred at room temperature for 1 hour. Ice water and conc. HCl was added to the reaction mixture and precipitated crystals were collected by filtration to obtain 0.05 g of 6-chloro-2,2-bis(fluoromethyl)-2H-1-benzopyran-4-carboxylic acid with a melting point of 151°–152° C.

MS m/z: 274 (M⁺)

(3) Using 6-chloro-2,2-bis(fluoromethyl)-2H-1-benzopyran-4-carboxylic acid, 6-chloro-2,2-bis(fluoromethyl)-N-methyl-2H-1-benzopyran-4-carboxamide with a melting point of 175°–176° C. was obtained according to the same method as in Example 7 (3).

NMR (CDCl$_3$)δ: 2.93(3H,d), 4.56(4H,d), 5.88(1H,brs), 5.96 (1H,s), 6.S2(1H,d), 7.21(1H,dd), 7.54(1H,d).

MS m/z: 287 (M⁺)

Example 53

6-Chloro-N-(2-cyanoethyl)-2,2-bis(fluoromethyl)-2H-1-benzopyran-4-carboxamide

Using 6-chloro-2,2-bis(fluoromethyl)-2H-1-benzopyran-4-carboxylic acid, 6-chloro-N-(2-cyanoethyl)-2,2-bis(fluoromethyl)-2H-1-benzopyran-4-carboxamide with a melting point of 134°–136° C. was obtained according to the same method as in Example 10.

NMR (CDCl$_3$)δ: 2.72(2H,t), 3.64(2H,q), 4.54(4H,d), 6.01 (1H,s), 6.57(1H,brs), 6.82(1H,d), 7.18(1H,dd), 7.51(1H,d).

MS m/z: 326 (M⁺)

Excellent activities of the compound of the present invention on the K⁺ channel will now be demonstrated below by way of Test Examples.

Test Example 1

Test with Excised Aorta of Rat

The thoracic aorta was excised from a male Sprague Dawley rat (450 to 600 g) and cut into 2 mm wide ring preparations. Each preparation was suspended in 10 ml of an organ bath containing a Krebs-Henseleit solution (NaCl: 119; KCl: 4.8; CaCl$_2$·2H$_2$O: 2.53; KH$_2$PO$_4$: 1.2; MgSO$_4$·7H$_2$O: 1.2; NaHCO$_3$: 24.8; glucose: 10 (mM); 37° C.) under a tension of 2 g, and a mixed gas of 95% O$_2$ and 5% CO$_2$ was bubbled therethrough. Isometric contractions of the preparation were recorded by means of an FD pick-up. After equilibrium was reached in 1 to 1.5 hours, 30 mM KCl was added to cause a tissue contraction. The activity of a test compound to relax a lasting contraction following the KCl addition was evaluated by obtaining a 50% inhibitory concentration (IC$_{50}$).

The compounds of the present invention obtained in the foregoing Examples and, for comparison, Cromakalim were used as test compounds. The results obtained are shown in Table 2 below.

Test Example 2

Test with Guinea Pig Tracheal Muscle

The trachea was excised from a male Hartley guinea pig (450 to 550 g) to make chain preparations. The preparation was suspended In a bath containing the same Krebs-henseleit solution as used in Test Example 1 (37° C.) through which a mixed gas of 95% O$_2$ and 5% CO$_2$ was bubbled. Isometric contractions of the preparation were recorded under a tension of 1 g. The relaxing activity of 1 mM aminophylline on spontaneous tension being taken as 100%, a concentration of a test compound exhibiting 50% relaxing activity (IC$_{50}$) was obtained.

The same test compounds as used in Test Example 1 were used. The results obtained are shown in Table 2.

TABLE 2

| Ex. No. | Rat Aorta IC$_{50}$ (M) | Guinea Pig Tracheal Muscle IC$_{50}$ (M) |
| --- | --- | --- |
| 1(2) | 5.9 × 10⁻⁸ | 8.6 × 10⁻⁸ |
| 2 | 1.7 × 10⁻⁸ | 2.9 × 10⁻⁸ |
| 3 | 9.7 × 10⁻⁸ | 2.6 × 10⁻⁷ |
| 7 | 6.0 × 10⁻⁹ | 1.0 × 10⁻⁸ |
| 8 | 2.8 × 10⁻¹⁰ | 3.0 × 10⁻⁹ |
| 9 | 1.4 × 10⁻⁸ | 4.1 × 10⁻⁸ |
| 10 | 2.1 × 10⁻⁹ | 5.0 × 10⁻⁹ |
| Cromakalim | 1.8 × 10⁻⁷ | 7.9 × 10⁻⁷ |

Test Example 3

Study on Antiasthmatic Activity

A mid-line incision was made in the neck of a male hartley guinea pig (600 to 800 g, CRJ) under anesthesia with phenobarbital (40 mg/kg, i.p.). The trachea, the left carotid vein, and the left carotid artery were exposed, and a cannula was inserted into each of them. The inner pressure of the respiratory tract was measured while applying artificial respiration through the tracheal cannula. The blood pressure was measured through the arterial cannula, and the heart rate was determined from the pulse. Pentobarbital for anesthesia maintenance was continuously administered through the venous cannula. A mid-line incision was made on the abdomen to expose the duodenum, and a canuula for intraduodenal administration was inserted thereinto. After the postoperative convalescene of 30 to 60 minutes, histamine (5 to 10 μg/kg) was intravenously administered every 10 minutes. After it was confirmed that a respiratory tract inner pressure rise reaction was stably obtained, a test compound in the form of a 0.3% CMC suspension was intraduodenally administered. The histamine dose was so selected that the respiratory tract inner pressure might rise to 20 to 40 cmH$_2$O after every intravenous administration. After administration of the test compound, intrvenous administration of histamine at 10 minutes intervals was continued. The histamine-induced increase in respiratory tract inner pressure after the administration of the test compound was compared with that before the administration.

The activity of the test compound, expressed in terms of dose level required for 50% inhibition of the histamine-induced increase in respiratory tract inner pressure (ED$_{50}$, mg/kg), is shown in Table 3 below.

TABLE 3

| Ex. No. | ED$_{50}$ (mg/kg) |
| --- | --- |
| 1(2) | 0.1 |
| 7 | 0.01 |
| Cromakalim | 1.0–3.0 |

UTILITY OF THE INVENTION IN INDUSTRY

The novel compounds of the present invention have excellent K⁺ channel opening activity and are therefore expected to make great contribution to the art, such as medical compositions utilizing K⁺ channel activation (e.g., anti-asthmatics).

We claim:

1. A benzopyran derivative represented by the following general formula (I):

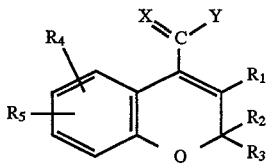

wherein $R_1$ represents a hydrogen atom $R_2$ and $R_3$ represent, in common with each other or independently, a substituted lower alkyl group containing a halogen atom as a substituent, simultaneously, though, $R_4$ and $R_5$ represent, in common with each other or independently, a hydrogen atom, a lower alkyl group, a lower haloalkyl group, a halogen atom, a lower alkoxy group, a lower haloalkoxy group, an amino group, an acylamino group, a nitro group, a cyano group, an ester group, a lower alkylsulfonyl group or an arylsulfonyl group, X represents =O, =S or =N—Z, wherein Z represents a hydrogen atom, a lower alkyl group, an aryl group, a hydroxyl group, a lower alkoxy group, a cyano group, a carbamoyl group or a sulfamoyl group, and Y represents —$NR_6R_7$, —$OR_8$ or —$SR_9$, wherein $R_6$ and $R_7$ represent, in common with each other or independently, a hydrogen atom, a hydroxyl group, a lower alkoxy group, a cyano group, an amino, a saturated or unsaturated lower alkyl group optionally containing a cyano group, an aryl group, a cycloalkyl group, a heteroaryl group, or $R_6$ and $R_7$, in combination, represent a heterocycle with a nitrogen atom, and $R_8$ and $R_9$ represent a hydrogen atom, a lower alkyl group or an aryl group.

2. A benzopyran derivative as claimed in claim 1 wherein $R_1$ represents a hydrogen atom, $R_2$ and $R_3$ represent, in common with each other or independently a substituted lower alkyl group containing a halogen atom as a substituent, $R_4$ and $R_5$ represent, in common with each other or independently, a hydrogen atom, a lower haloalkyl group, a halogen atom, an amino group, a nitro group or a cyano group, X represents =O, =S, or =N—CN, and Y represents —$NR_6R_7$ or —$OR_8$, wherein $R_6$ and $R_7$ represent, in common with each other or independently, a hydrogen atom, or a saturated lower alkyl group optionally containing a substituent, and $R_8$ represents a hydrogen atom or a lower alkyl group.

3. A benzopyran derivative as claimed in claim 1 wherein $R_4$ or $R_5$ represents a nitro group at the 6-position.

4. A benzopyran derivative as claimed in claim 3 wherein $R_4$ or $R_5$ represents a nitro group at the 6-position, X represents =O, =S, or =N—CN, and Y represents —$NR_6R_7$ wherein $R_6$ and $R_7$ represent, in common with each other or independently, a hydrogen atom, a lower alkyl group or a lower alkyl group substituted with a cyano group.

5. A $K^+$ channel activator composition comprising a benzopyran derivative represented by the following general formula (I):

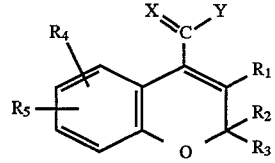

wherein $R_1$ represents a hydrogen atom, $R_2$ and $R_3$ represent, in common with each other or independently, a substituted lower alkyl group containing a halogen atom as a substituent, $R_4$ and $R_5$ represent, in common with each other or independently, a hydrogen atom, a lower alkyl group, a lower haloalkyl group, a halogen atom, a lower alkoxy group, a lower haloalkoxy group, an amino group, an acylamino group, a nitro group, a cyano group, an ester group, a lower alkylsulfonyl group or an arylsulfonyl group, X represents =O, =S or =N—Z, wherein Z represents a hydrogen atom, a lower alkyl group, an aryl group, a hydroxyl group, a lower alkoxy group, a cyano group, a carbamoyl group or a sulfamoyl group, and Y represents —$NR_6R_7$, —$OR_8$ or —$SR_9$, wherein $R_6$ and $R_7$ represent, in common with each other or independently, a hydrogen atom, a hydroxyl group, a lower alkoxy group, a cyano group, an amino group, a saturated or unsaturated lower alkyl group optionally containing a cyano group, an aryl group, a cycloalkyl group, a heteroaryl group, or $R_6$ and $R_7$, in combination, represent a heterocycle with a nitrogen atom, and $R_8$ and $R_9$ represent a hydrogen atom, a lower alkyl group or an aryl group.

6. A benzopyran derivative according to claim 1 of the formula (II):

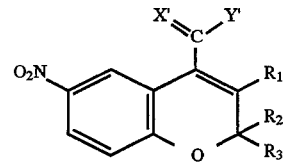

wherein

X' represents =O, =S or =N—CN, and

Y' represents —$NR_{10}R_{11}$, and one of $R_{10}$ and $R_{11}$ is hydrogen and the other of $R_{10}$ and $R_{11}$ is a lower alkyl or a cyano substituted lower alkyl.

7. A benzopyran derivative according to claim 2 wherein $R_4$ is $NO_2$, halogen, $NH_2$, $CF_3$, $C_2F_5$, $C_3F_7$ or CN; and $R_5$ is H or Cl.

* * * * *